(12) United States Patent
Cao et al.

(10) Patent No.: US 9,533,879 B2
(45) Date of Patent: Jan. 3, 2017

(54) INTEGRATED ANALYSIS DEVICES AND RELATED FABRICATION METHODS AND ANALYSIS TECHNIQUES

(75) Inventors: Han Cao, Philadelphia, PA (US); Michael D. Austin, Philadelphia, PA (US); Parikshit A. Deshpande, Princeton, NJ (US); Mark Kunkel, Lawrenceville, NJ (US); Alexey Y. Sharonov, Hamden, CT (US); Michael Kochersperger, Princeton, NJ (US)

(73) Assignee: BioNano Genomics, Inc., Philadelphia, PA (US)

( * ) Notice: Subject to any disclaimer, the term of this patent is extended or adjusted under 35 U.S.C. 154(b) by 1157 days.

(21) Appl. No.: 12/996,410

(22) PCT Filed: Jun. 5, 2009

(86) PCT No.: PCT/US2009/046427
§ 371 (c)(1),
(2), (4) Date: Feb. 16, 2011

(87) PCT Pub. No.: WO2009/149362
PCT Pub. Date: Dec. 10, 2009

(65) Prior Publication Data
US 2011/0296903 A1    Dec. 8, 2011

Related U.S. Application Data

(60) Provisional application No. 61/059,399, filed on Jun. 6, 2008.

(51) Int. Cl.
*G01N 21/64*    (2006.01)
*B81C 1/00*     (2006.01)
(Continued)

(52) U.S. Cl.
CPC ...... *B81C 1/00119* (2013.01); *B01L 3/502761* (2013.01); *B01L 2200/0663* (2013.01);
(Continued)

(58) Field of Classification Search
CPC . G01N 11/00; G01N 37/00; G01N 2021/6439
(Continued)

(56) References Cited

U.S. PATENT DOCUMENTS 6,635,163 B1 * 10/2003 Han et al. .............. 204/450
7,069,952 B1    7/2006 McReynolds et al.
(Continued)

FOREIGN PATENT DOCUMENTS

CN    1339610      3/2002
EP    1 371 990    12/2003
(Continued)

OTHER PUBLICATIONS

Mannion et al., Conformational Analysis of Single DNA Molecules Undergoing Entropically Induced Motion in Nanochannels, Biophysical Journal, vol. 90, pp. 4538-4545 (2006).
(Continued)

*Primary Examiner* — Laura Martin
*Assistant Examiner* — Alex Devito
(74) *Attorney, Agent, or Firm* — Knobbe, Martens, Olson & Bear, LLP

(57) ABSTRACT

Provided are integrated analysis devices having features of macroscale and nanoscale dimensions, and devices that have reduced background signals and that reduce quenching of fluorophores disposed within the devices. Related methods of manufacturing these devices and of using these devices are also provided.

24 Claims, 21 Drawing Sheets

(51) Int. Cl.
 *B01L 3/00* (2006.01)
 *G01N 21/03* (2006.01)
(52) U.S. Cl.
 CPC ... *B01L 2200/0689* (2013.01); *B01L 2200/10* (2013.01); *B01L 2300/0816* (2013.01); *B01L 2300/0851* (2013.01); *B01L 2300/0858* (2013.01); *B01L 2300/0864* (2013.01); *B01L 2300/0887* (2013.01); *B01L 2300/168* (2013.01); *B01L 2400/043* (2013.01); *B01L 2400/0415* (2013.01); *B01L 2400/0442* (2013.01); *B01L 2400/0487* (2013.01); *B01L 2400/086* (2013.01); *B81B 2201/058* (2013.01); *B81C 2201/019* (2013.01); *G01N 2021/0346* (2013.01); *G01N 2021/6439* (2013.01); *Y10T 29/4981* (2015.01)
(58) Field of Classification Search
 USPC .............................. 73/64.56, 863.41, 863.82
 See application file for complete search history.

(56) References Cited

U.S. PATENT DOCUMENTS

| | | | |
|---|---|---|---|
| 7,670,770 | B2 | 3/2010 | Chou et al. |
| 2003/0049563 | A1 | 3/2003 | Iida et al. |
| 2004/0033515 | A1 | 2/2004 | Cao et al. |
| 2004/0121356 | A1 | 6/2004 | Yamagata et al. |
| 2004/0197843 | A1 | 10/2004 | Chou et al. |
| 2005/0112606 | A1 | 5/2005 | Fuchs et al. |
| 2006/0065528 | A1 | 3/2006 | Lopez et al. |
| 2006/0275911 | A1* | 12/2006 | Wang et al. ............ 436/106 |

FOREIGN PATENT DOCUMENTS

| | | |
|---|---|---|
| JP | 2000-111477 | 4/2000 |
| JP | 2004-45357 | 2/2004 |
| JP | 2005-505754 | 2/2005 |
| JP | 2005-533636 | 11/2005 |
| JP | 2006-26452 | 2/2006 |
| JP | 2007-278906 | 10/2007 |
| WO | WO 93/22058 | 11/1993 |
| WO | WO 98/35012 | 8/1998 |
| WO | WO 00/10015 | 2/2000 |
| WO | WO 00/10015 A1 | 2/2000 |
| WO | WO01/13088 | 2/2001 |
| WO | WO 02/65138 | 2/2002 |
| WO | WO 02/065138 | 8/2002 |
| WO | WO 03/106693 | 12/2003 |
| WO | WO 2004/091795 | 10/2004 |
| WO | WO2006/096123 | 9/2006 |
| WO | WO 2006/101851 | 9/2006 |
| WO | WO 2006/117541 | 11/2006 |
| WO | WO2007/134120 | 11/2007 |

OTHER PUBLICATIONS

International Search Report and Written Opinion dated Aug. 11, 2010 for PCT Application PCT/US09/046427.
Examination Report dated Mar. 28, 2012 for European Patent Application No. 09759520.1.
Office Action dated Feb. 5, 2013 for Japanese Patent Application No. 2011-512694.
Search Report dated Mar. 12, 2012 for Singapore Patent Application No. 201008920-9.
Final Examination Report dated Dec. 4, 2012 for Singapore Patent Application No. 201008920-9.
Japanese office action dated Dec. 17, 2013 for Japanese Patent Application No. 2011-512694.
Chinese Office Action dated Mar. 7, 2014 for Chinese Patent Application No. 200980130482.X.
Chinese Office Action dated Aug. 15, 2013 for Chinese Patent Application No. 200980130482.X.
Australian Office Action dated Apr. 9, 2014 for Australian Patent Application No. 2009256064.
Abad et al., 2008, Design and fabrication using nanoimprint lithography of a nanofluidic device for DNA stretching applications, Microelectronic Engineering, 85:818-821.
Cao, Oct. 14, 2002, Gradient nanostructures for interfacing microfluidics and nanofluidics, Gradient nanostructures for interfacing microfluidics and nanofluidics, 81(16):3058-3060.
Cho., Mar. 13, 2008, Fabrication of silicon dioxide nanochannel arrays without nanolithography for manipulation of DNA mo, Microelectronic Engineering, 85:1275-1277.
Kaji et al., 2004, Separation of long DNA molecules by quartz nanopillar chips under a direct current electric field, Anal. Chem., 76(1):15-22.
Reccius et al., Dec. 31, 2005, Compression and free expansion of single dna molecules in nanochannels, Physical Review Letters, 95:268101-1-268101-4.
Patent Examination Report No. 2 in Australian patent application No. 2009256064.
Official Action dated Jun. 23, 2015 in Canadian patent application No. 2,727,095.
Examination Report dated Oct. 13, 2015 in European patent application No. 09759520.1.
Final Decision of Rejection dated Jul. 15, 2014 in Japanese patent application No. 2011-512694.
Pre-Trial Patentability Report dated Jan. 14, 2015 in Japanese patent application No. 2011-512694.
Office Action dated Jan. 30, 2015 for Korean patent application No. 10-2011-7000192.
Notice of Final Rejection dated Sep. 21, 2015 for Korean patent application No. 10-2011-7000192.
Pre-Trial Patentability Report dated Jul. 7, 2015 in Japanese patent application No. 2011-512694.
Office Action dated Nov. 17, 2015 in Japanese patent application No. 2011-512694.
Office Action dated Oct. 27, 2015 in Japanese patent application No. 2014-233087.
Canadian Office Action dated Jun. 27, 2016 for Canadian Patent Application No. 2,727,095.
Guo et al. Dec. 3, 2003, Fabrication of size-controllable nanofluidic channels by nanoimprinting and its application for DNA stretching, Nano Letters, 4(1):69-73.
Huh et al., May 7, 2007, Tuneable elastomeric nanochannels for nanofluidic manipulation, Nature Materials, 6:424-428.
Patent Examination Report No. 1 dated Jul. 25, 2016 in Australian patent application No. 2015205826.
Official Action dated Jun. 27, 2016 in Canadian patent application No. 2,727,095.
Office Action dated Jun. 22, 2016 in Chinese Patent Application No. 201410462892.7.
Office Action dated Sep. 13, 2016 in Japanese patent application No. 2014-233087.

* cited by examiner

Region of nanochannels

INTEGRATED ANALYSIS DEVICES AND RELATED FABRICATION METHODS AND ANALYSIS TECHNIQUES

CROSS-REFERENCE TO RELATED APPLICATIONS

This application is the National Stage of International Application No. PCT/US2009/046427, filed Jun. 5, 2009, which claims the benefit of U.S. application No. 61/057,917 filed Jun. 6, 2008, the disclosures of which are incorporated herein by reference in their entireties for all purposes.

STATEMENT REGARDING FEDERALLY SPONSORED R&D

This invention was made with government support under Grant No. HG004199 awarded by National Institutes of Health. The U.S. Government has certain rights in this invention.

TECHNICAL FIELD

The present invention relates to the field of nanofluidics and to the field of solid-state optical analysis devices.

BACKGROUND

One of the challenges in current biomedical analysis is to fully account for the the complexity of biological samples that may have a great deal of heterogeneity, and in which samples no two objects are exactly alike. The minority population of cells or molecules in a given sample is often the most clinically relevant portion to the pathophysiological state of the patients.

Conventional bulk solution assays can average out and obscure small but salient features of a heterogeneous sample preventing the early discovery of the disease causal molecules, features and events. As molecular biology techniques have evolved, there is increasing interest in analyzing progressively smaller samples with ever-increasing resolution and precision.

The world of single molecule level biology is inherently at the micron- and below scale. One challenge in the field is fabrication of high quality micro- and nanofluidic structures on solid state materials that are compatible with existing fabrication processes. The optical purity of the inner surface of a device has a paramount importance in nanofluidics designed for single molecule level fluorescent imaging, because optical background contamination generates excessive autofluorescent noise that reduces the effectiveness of the fluidic device. Optical purity, however, is not considered an important aspect in conventional semiconductor fabrication.

An additional challenge facing the field is moving molecules or other targets from a macroscale environment (e.g., pipettes) to micro- or nano-scale regions, as well as moving such molecules and associated media from the micro- or nano-scale regions to macro-scale waste outlets or sample collection chambers for further downstream analysis.

Such devices must accommodate features having sizes ranging from centimeters down to single digit nanometers (a seven orders of magnitude difference), which represents a tremendously broad range of length scales to integrate together in a way that allows for controllable and leak-free transport.

Along with the issues presented by transporting biological and other targets is the challenge detecting light emitting labels on such targets (e.g., molecules or cellular components of interest), which detection may be performed on the target while the target is disposed in an enclosed channel. Such detection has many practical applications, particularly in the field of nanofluidics.

Of particular importance to such detection is the signal-to-background ratio (SBR) (also referred to as signal-to-noise ration, S/N) of the label's electromagnetic signal to that of the background signal of the device in which the label is contained. Maximizing the SBR by reducing the background enhances the value of a given system by increasing the dynamic range of that system. The value is further increased by a device in which the electromagnetic radiation constituting the device's background signal is reduced across the broadest possible spectral range.

Certain substrates, such as silicon, quench fluorescent emission when imaging fluorophores on a flat, open silicon substrate, as is commonly done in microarray-based applications. To prevent this quenching, a substrate coating is typically employed to reduce or eliminate quenching. However, when incorporated into a bonded fluidic device with confined channels, the coating material may often increase the background signal of the device, which in turn degrades the device performance, and effectively exchanges one problem (quenching) for another (increased background).

Accordingly, there is a need in the art for devices that exhibit a comparatively low level of background signal while also limiting the quenching of fluorophores or other labels present in the device. There is also a need in the art for related methods of fabricating devices having such characteristics.

SUMMARY

In meeting the described challenges, the claimed invention first provides analysis devices, comprising a first substrate; a second substrate; a first inlet port extending through at least a portion of the first substrate, the second substrate, or both, so as to place a first interconnector channel in fluid communication with the environment exterior to the analysis device; and a first front-end branched channel region, comprising at least a primary channel characterized as having a cross-sectional dimension in the range of from less than about 10,000 nm and at least two secondary channels, placing the first interconnector channel into fluid communication with a nanochannel analysis region, the nanochannel analysis region comprising at least one nanochannel characterized as having a cross-sectional dimension less than that of the primary channel, and wherein the ratio of the cross-sectional dimensions of the primary channel to the nanochannel is in the range of from about 100 to about 10,000.

Also provided are methods of fabricating analysis devices, the methods including bonding a first substrate and a second substrate, at least one of the substrates comprising at least one channel having a width in the range of from about 10 nm to about 10,000 nm, the bonding giving rise to an enclosed conduit disposed between the substrates, the enclosed conduit being capable of transporting a fluid therethrough.

Further provided are methods of analysis, comprising translocating a macromolecule through at least two channels of successively decreasing width such that at least a portion of the macromolecule is elongated while disposed in the narrowest of the channels; the ratio of the widths of the widest and narrowest channels is in the range of from about 1 to about $10^6$; detecting a signal from the macromolecule while it resides in a first region of a channel having a width of from 10 nm to about 1000 nm; and correlating the signal to a property of the macromolecule.

Further provided are analysis devices, comprising a first substrate and a second substrate, the first and second substrates defining a channel disposed between the substrates, at least one of the first or second substrates permitting at least partial passage of electromagnetic radiation characterized as having at least one wavelength in the range of from about 10 nm to about 2500 nm; a first thin film surmounting at least a portion of the first substrate, the second substrate, or both, at least a portion of the first thin film defining at least a portion of a channel disposed between the first and second substrates, and the first thin film giving rise to a reduced background signal of the device when the device is illuminated by electromagnetic radiation having a wavelength in the range of from about 10 nm to about 2500 nm, relative to an identical device without said first thin film.

Additionally provided are analysis devices, comprising a substrate configured so as to define a channel enclosed within the substrate, the substrate being transparent to electromagnetic radiation having at least one frequency component in the range of from about 10 nm to about 2500 nm.

Further provided are methods of fabricating an analysis device, comprising disposing a first substrate, a second substrate, and a first thin film layer so as to define a channel disposed between the first and second substrates, the first thin film layer being selected such that said layer reduces the background signal of the device when the device is illuminated by electromagnetic radiation having a wavelength in the range of from about 10 nm to about 2500 nm, relative to an identical device without said first thin film; and bonding the first thin film layer to the first substrate, the second substrate, or both.

Also provided are methods of fabricating an analysis device, comprising disposing a sacrificial template within a workpiece comprising a material that is transparent to electromagnetic radiation having a wavelength in the range of from about 10 nm to about 5000 nm; removing at least a portion of the sacrificial template so as to give rise to a channel disposed within the workpiece, at least a portion of the channel having a cross-sectional dimension in the range of from about 5 nm to about 5000 nm.

Further provided are methods of analyzing a fluorescently labeled molecule, comprising placing at least a portion of the fluorescently labeled molecule into a channel within an analysis device, the analysis device having at least a first substrate, a second substrate, and a first thin film configured to give rise to the channel being disposed between the first and second substrates, the first thin film bonded to the first substrate, the second substrate, or both, the fluorescently labeled molecule capable of emitting electromagnetic radiation of an emission wavelength when the sample is illuminated by electromagnetic radiation of an excitation wavelength in the range of from about 10 nm to about 2500 nm, the first thin film reducing the background signal of the device when the device is illuminated by electromagnetic radiation of the excitation wavelength, relative to an identical device without said first thin film, and collecting electromagnetic radiation of the emission wavelength emitted from the fluorescently labeled molecule.

BRIEF DESCRIPTION OF THE DRAWINGS

The summary, as well as the following detailed description, is further understood when read in conjunction with the appended drawings. For the purpose of illustrating the invention, there are shown in the drawings exemplary embodiments of the invention; however, the invention is not limited to the specific methods, compositions, and devices disclosed. In addition, the drawings are not necessarily drawn to scale. In the drawings.

DETAILED DESCRIPTION OF ILLUSTRATIVE EMBODIMENTS

Figure 1:
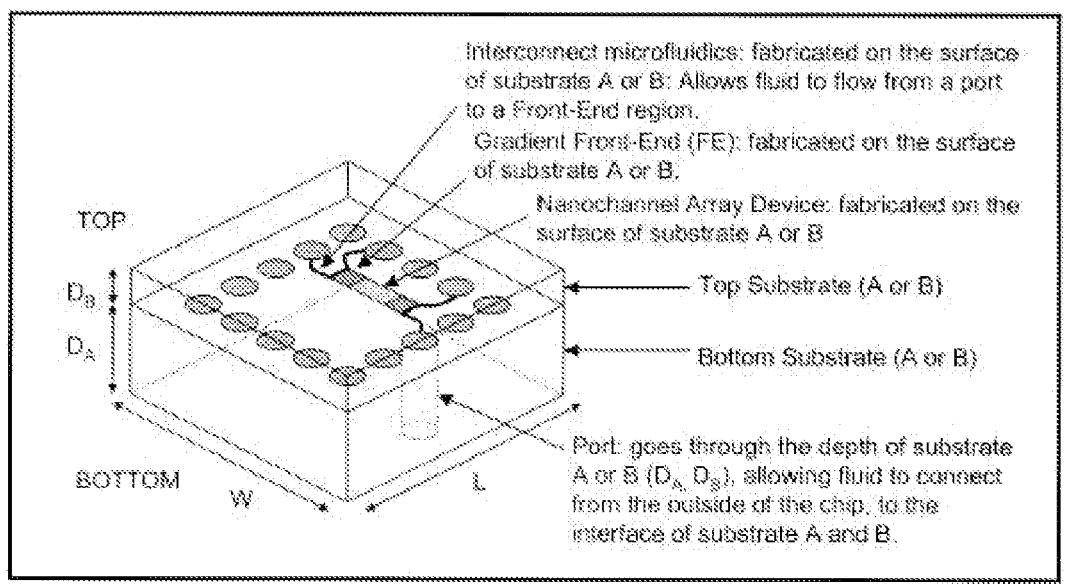
FIG. 1 depicts a schematic view of a device according to the claimed invention.

The present invention may be understood more readily by reference to the following detailed description taken in connection with the accompanying figures and examples, which form a part of this disclosure. It is to be understood that this invention is not limited to the specific devices, methods, applications, conditions or parameters described and/or shown herein, and that the terminology used herein is for the purpose of describing particular embodiments by way of example only and is not intended to be limiting of the claimed invention. Also, as used in the specification including the appended claims, the singular forms "a," "an," and "the" include the plural, and reference to a particular numerical value includes at least that particular value, unless the context clearly dictates otherwise. The term "plurality", as used herein, means more than one. When a range of values is expressed, another embodiment includes from the one particular value and/or to the other particular value. Similarly, when values are expressed as approximations, by use of the antecedent "about," it will be understood that the particular value forms another embodiment. All ranges are inclusive and combinable.

It is to be appreciated that certain features of the invention which are, for clarity, described herein in the context of separate embodiments, may also be provided in combination in a single embodiment. Conversely, various features of the invention that are, for brevity, described in the context of a single embodiment, may also be provided separately or in any subcombination. Further, reference to values stated in ranges include each and every value within that range.

TERMS

As used herein, "fluidic element" means a feature capable of containing or admitting a fluid, such as a channel, a groove, a trench, an aperture, a portal, a hole, a via, and the like.

As used herein, "cross-sectional dimension" means a width, a diameter, a depth, or other across-wise measurement.

The claimed invention first provides analysis devices. These devices suitably include, inter alia, a first substrate, and a second substrate. Suitable substrate materials are described elsewhere herein, and include, e.g., silicon, glass, and quartz.

The devices also include a first inlet port extending through at least a portion of the first substrate, the second substrate, or both, so as to place a first interconnector channel in fluid communication with the environment exterior to the analysis device.

Also present in the devices is a first front-end branched channel region, which region includes at least a primary channel characterized as having a cross-sectional dimension in the range of from less than about 10,000 nm and at least two secondary channels, placing the first interconnector channel into fluid communication with a nanochannel analysis region. Branched channel arrangements are shown in, e.g., FIGS. 5(b), 7(c) and 8(c), which figures show primary channels divided into smaller secondary channels.

The nanochannel analysis region suitably includes at least one nanochannel characterized as having a cross-sectional dimension that is less than that of the primary channel. The ratio of the cross-sectional dimensions of the primary channel to the nanochannel is in the range of from about 100 to about 10,000, or from about 1000 to about 5000, or even about 2000.

Substrates may be of many different materials. The first substrate, the second substrate, or both is suitably silicon, SiGe, Ge, strained silicon, GeSbTe, AlGaAs, AlGaInP, AlGaN, AlGaP, GaAsP, GaAs, GaN, GaP, InAlAs, InAlP, InSb, GaInAlAs, GaInAlN, GaInAsN, GaInAsP, GaInAs, GaInN, GaInP, GaSb, InN, InP, CdSe, or CdTe. Zinc compounds, such as zinc selenide (ZnSe), HgCdTe, ZnO, ZnTe, and zinc sulfide (ZnS) are all useful.

A listing of substrate materials also includes aluminum, aluminum oxide, stainless steel, Kapton™, metal, ceramic, plastic, polymer, sapphire, silicon carbide, silicon on insulator (SOI), astrosital, barium borate, barium fluoride, sillenite crystals BGO/BSO/BTO, bismuth germanate, calcite, calcium fluoride, cesium iodide, $FeliNbO_3$, fused quartz, quartz, fused silica, glass, $SiO_2$, gallium, gadolinium garnet, potassium dihydrogen phosphate (KDP), thalium bromoiodide (KRS-5), potassium titanyl phosphate, lead molibdate, lithium fluoride, lithium iodate, lithium niobate, lithium tantalate, magnesium fluoride, potassium bromide, titanium dioixde, sodium chloride, tellurium dioxide, zinc selenide, spin-on glass, UV curable materials, soda lime glass, any compound above in hydrogenated form, stoichiometric variations of the above compounds, or any combinations thereof. In some embodiments, a substrate is optically opaque, in others, a substrate is essentially transparent to visible light or to at least one wavelength of electromagnetic radiation.

The first substrate suitable has a thickness in the range of from about 10 nm to about 10,000 nm, or from about 100 nm to about 1000 nm, or from about 200 nm to about 500 nm. The second substrate may have a thickness in the same range; the two substrates may of the same thickness or of different thicknesses.

An inlet port is suitably circular in cross-section (e.g., FIG. 1), although other profiles may be used. An inlet port suitably has a diameter or other cross-sectional dimension in the range of from about 5 microns to about 5000 microns, or from about 10 microns to about 100 microns, or about 50 microns. The inlet port may extent through the thickness of a substrate, or partially through the substrate. The port may be plugged or capped, and can also include a valve or other seal.

Outlet ports suitably have dimensions similar to those of inlet ports, although inlet and outlet ports on a given device need not be of the same dimensions. A port suitably extends through the entire thickness of a substrate, although inlets (and outlets) that extend through only a portion of a substrate may also be used.

An interconnector channel of the claimed invention suitably has a depth in the range of from about 100 nm to about 100 microns, or from about 500 nm to about 50 microns, or from about 1 micron to about 10 microns. The interconnector also suitably has a width in the range of from about 500 nm to about 1000 microns, or from about 1 micron to about 50 microns, or from about 10 microns to about 50 microns. Interconnect regions are shown in, e.g., FIG. 5.

Figure 5:
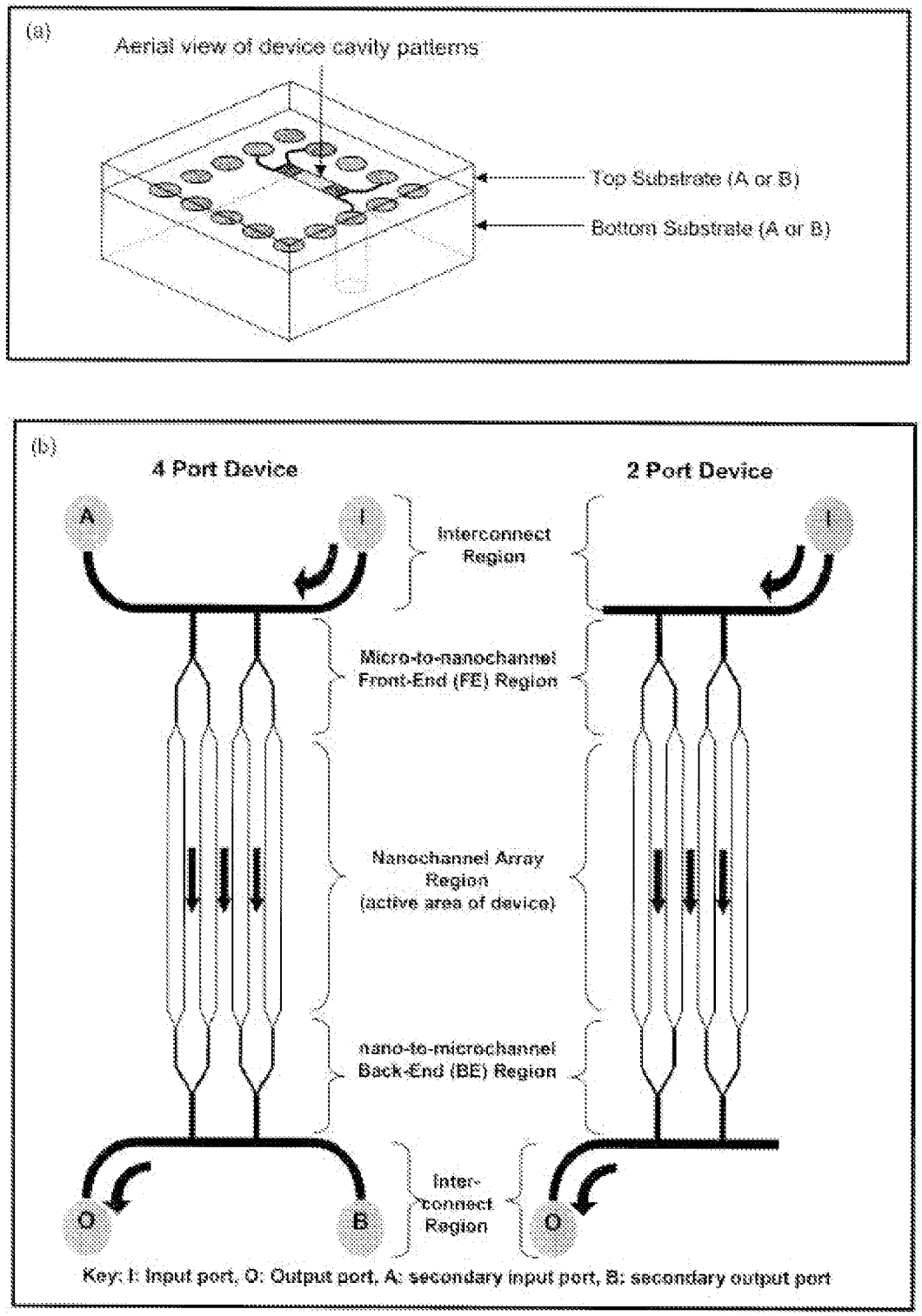
FIG. 5 depicts an exemplary nanodevices having 2 and 4 ports.
Figure 6:
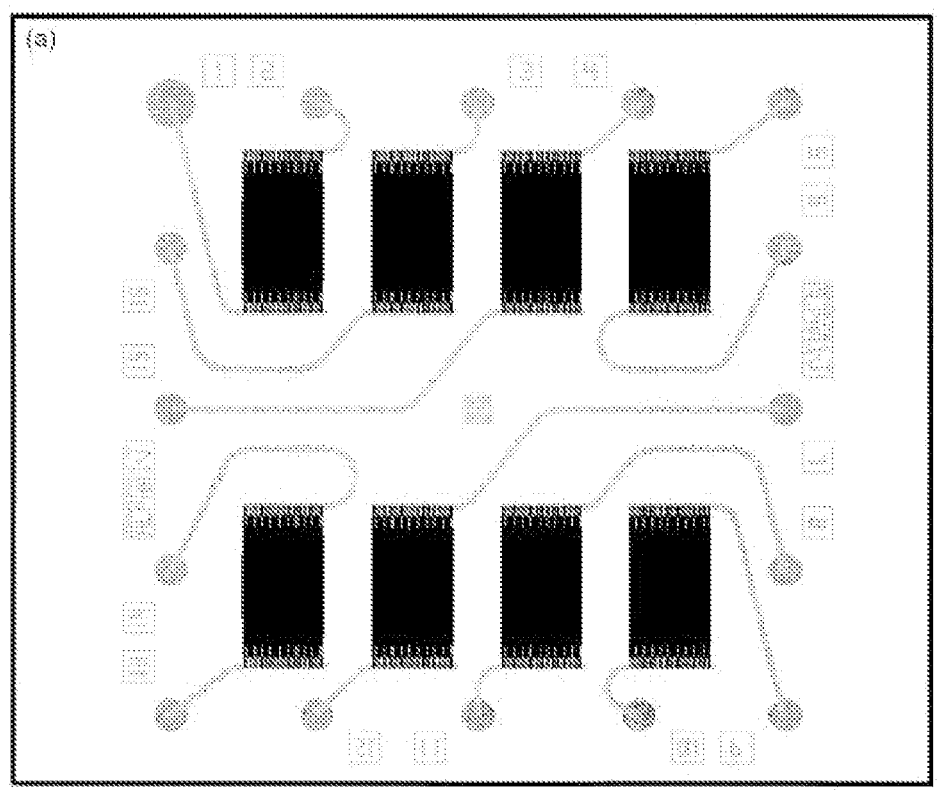
FIG. 6 depicts an example embodiment of a multi-port device design.
Figure 6:
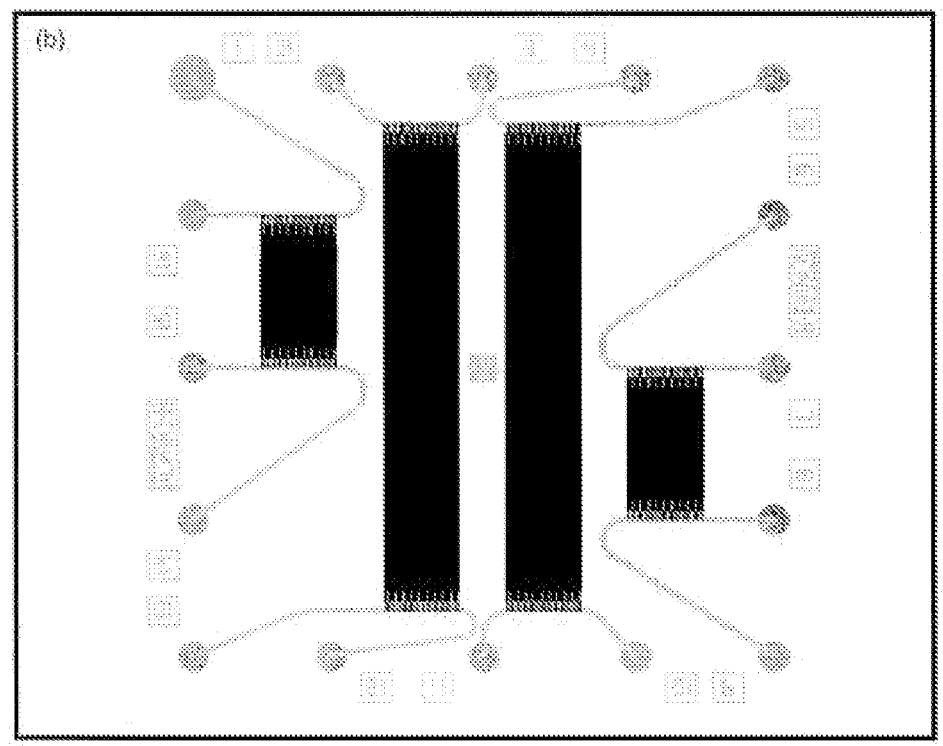

An interconnector may in some configurations connect two—or more—inlets, and may also be in fluid communication with one, two, three, or more primary channels of branched regions, as shown in FIG. 5. In some embodiments, the branched region is in direct fluid communication with the inlet port, without an intervening interconnector region.

In the branched (or furcated) regions of the claimed devices, the primary channel suitably has a width in the range of from about 10 nm to about 10,000 nm, or in the range of from about 50 nm to about 1000 nm, or in the range of from 75 nm to about 200 nm. The optimal with of a primary channel will depend on the needs of the user.

Primary channels can have a depth in the range of from about 10 nm to about 1000 nm, or from about 50 nm to about 500 nm, or even from about 100 nm to about 200 nm.

Figure 7:
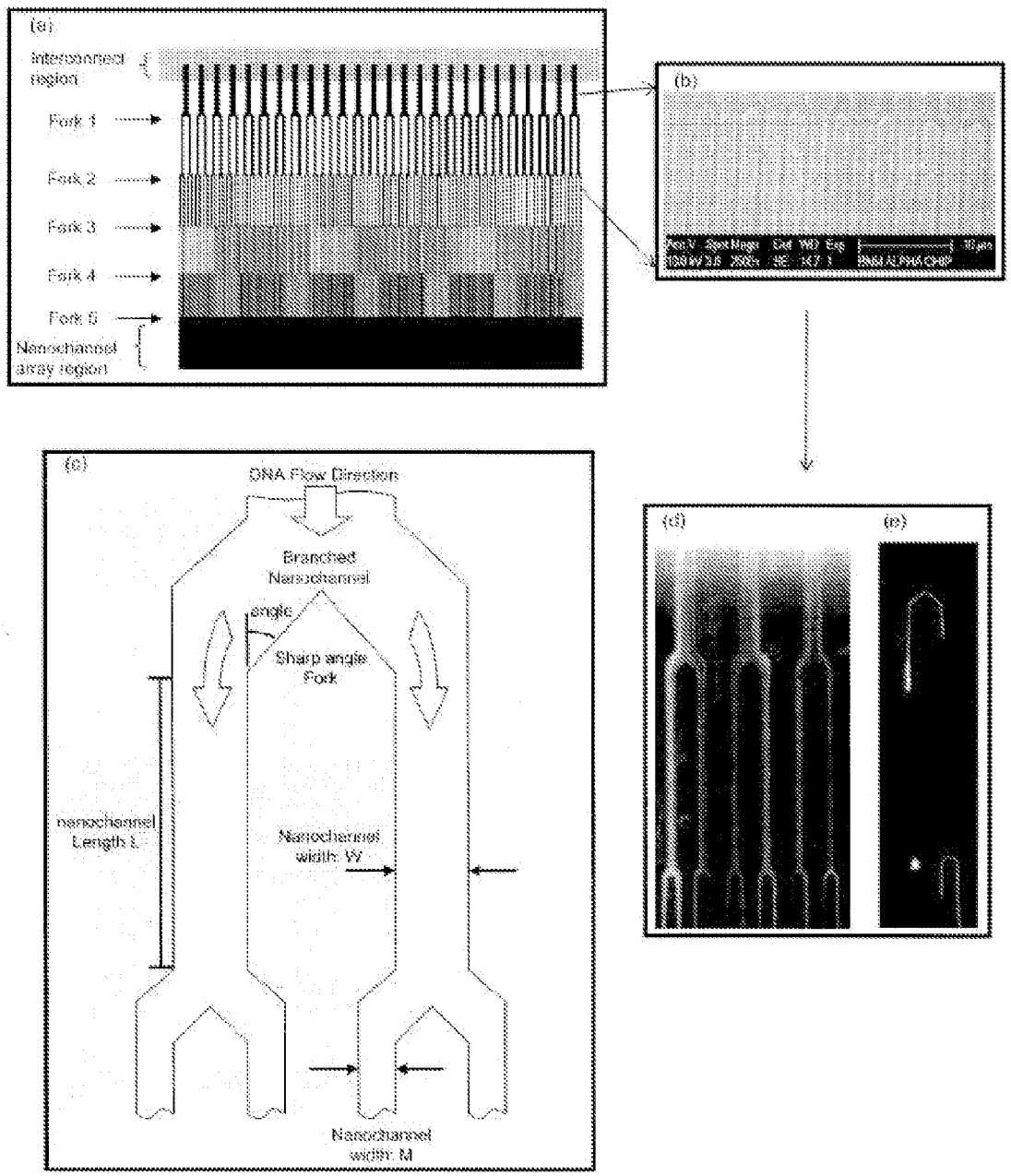
FIG. 7 depicts a multi-stage branched channel array according to the claimed invention.

The front-end branched channel region suitably includes a splitter structure that divides the primary channel into least two secondary channels, as shown in, e.g., FIG. 7. In some embodiments (see FIG. 7), the splitter structure includes at least one surface angled in the range of from about 0 and about 90 degrees relative to the centerline of the primary channel. In the non-limiting embodiment shown in FIG. 7, the splitter includes a surface angled between 0 ad 90 degrees relative to the centerline of the primary channel shown at the top of FIG. 7(c).

The width of a secondary channel in such embodiments is suitably in the range of from about 30% to about 70% of the width of the primary channel, or about 45% to 55% of the primary channel. In some embodiments, the cross-sectional area of a secondary channel is about 50% of the cross-sectional area of the primary channel. In other embodiments, one of the secondary channels differs in cross-sectional area, width, depth, or some combination thereof from the other secondary channel. In other embodiments, the secondary channels are of similar or even identical dimensions to each other.

A secondary channel may have a length in the range of from about 1 microns and about 500 microns, or from about 10 microns to about 100 microns. Secondary channels may have the same or different lengths.

In some embodiments (e.g., FIG. 7, FIG. 8), a secondary channel is divided into two tertiary channels by a splitter having at least one surface angled in the range of from about 0 and about 90 degrees relative to the centerline of the secondary channel. This is shown by the non-limiting embodiment of FIG. 7.

Figure 8:
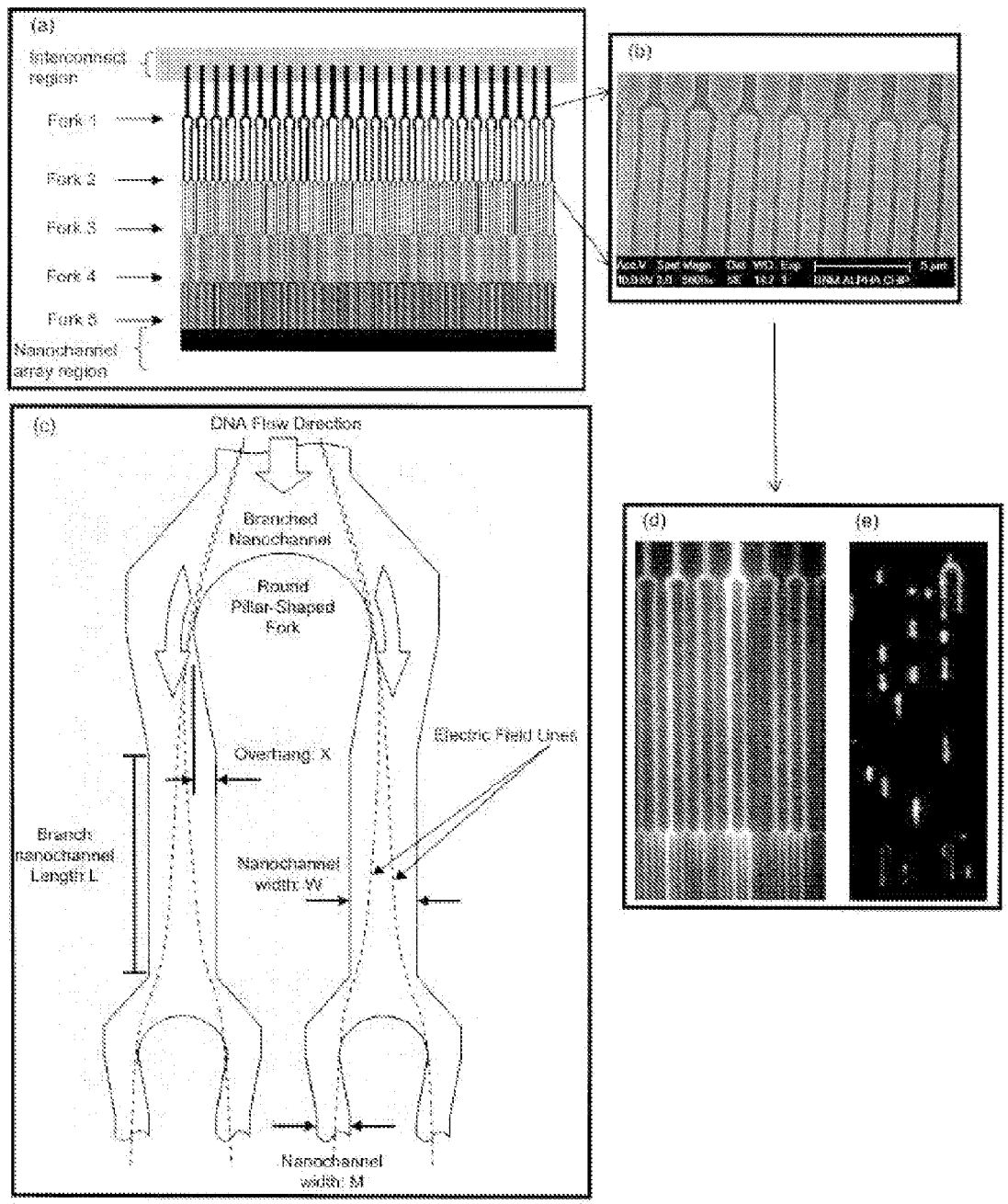
FIG. 8 illustrates a multi-level, branched, interconnected channel array.

In some configurations of the claimed invention, the splitter structure includes a contoured portion, such as that shown in FIG. 8. Such splitter structures are suitably configured such that a fluidborne body propelled through the primary channel by a gradient is essentially equally likely to enter either secondary channel downstream from the splitter structure, as shown in FIG. 8(c). As shown in that figure, the splitter is shaped and configured such that field lines of an electric field applied across the device will result in targets (e.g., DNA or other biopolymers) that pass through the region being distributed essentially equally across the four tertiary channels shown at the bottom of the figure.

The splitter may be configured so as to define an overhang that shields at least a portion of the secondary channel from the primary channel, as shown in FIG. 8. The overhang may be configured such that the overhang is in the range of from about 5% to about 50% of the width of the secondary channel.

The width of a secondary channel may be in the range of from about 30% to about 70% of the width of the primary channel, or even 50% of the primary channel. As described elsewhere herein, a secondary channel may have a cross-sectional area that is in the range of from about 30% to 70% of the cross-sectional area of the primary channel, or even about 50% of the cross-sectional area of the primary channel.

A nanochannel in the nanochannel analysis region of the claimed devices suitably has a width in the range of from about 1 nm to about 1000 nm, or from about 10 nm to about 100 nm, or even from about 50 nm to about 80 nm. The nanochannel can have a depth in the range of from about 10 nm to about 500 nm, or from about 20 nm to about 200 nm, or even from about 50 nm to about 100 nm.

Figure 10:
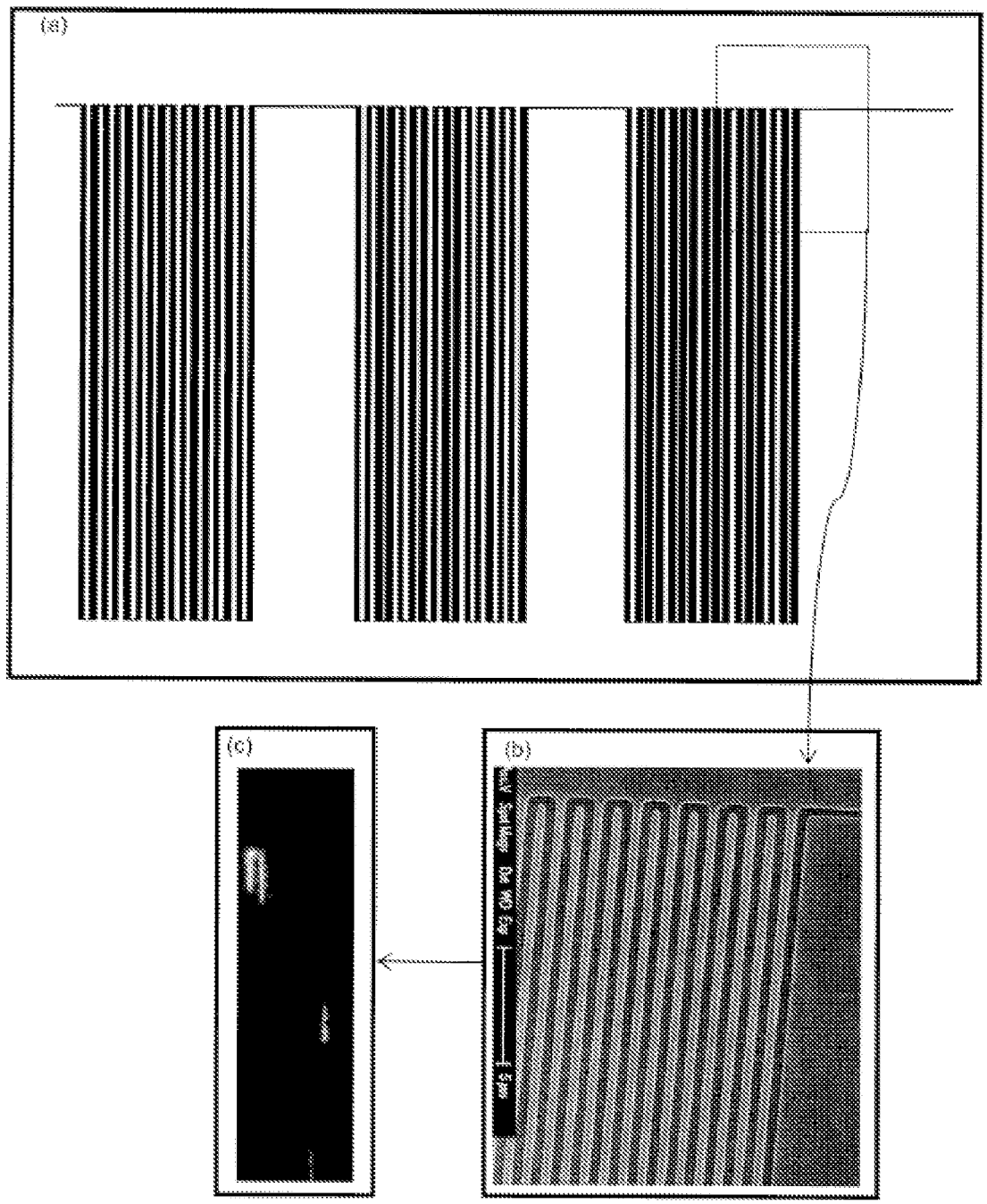
FIG. 10 depicts a design having a single long nanochannel arranged in a continuously connected, serial set of parallel nanochannels in a serpentine configuration.
Figure 11:
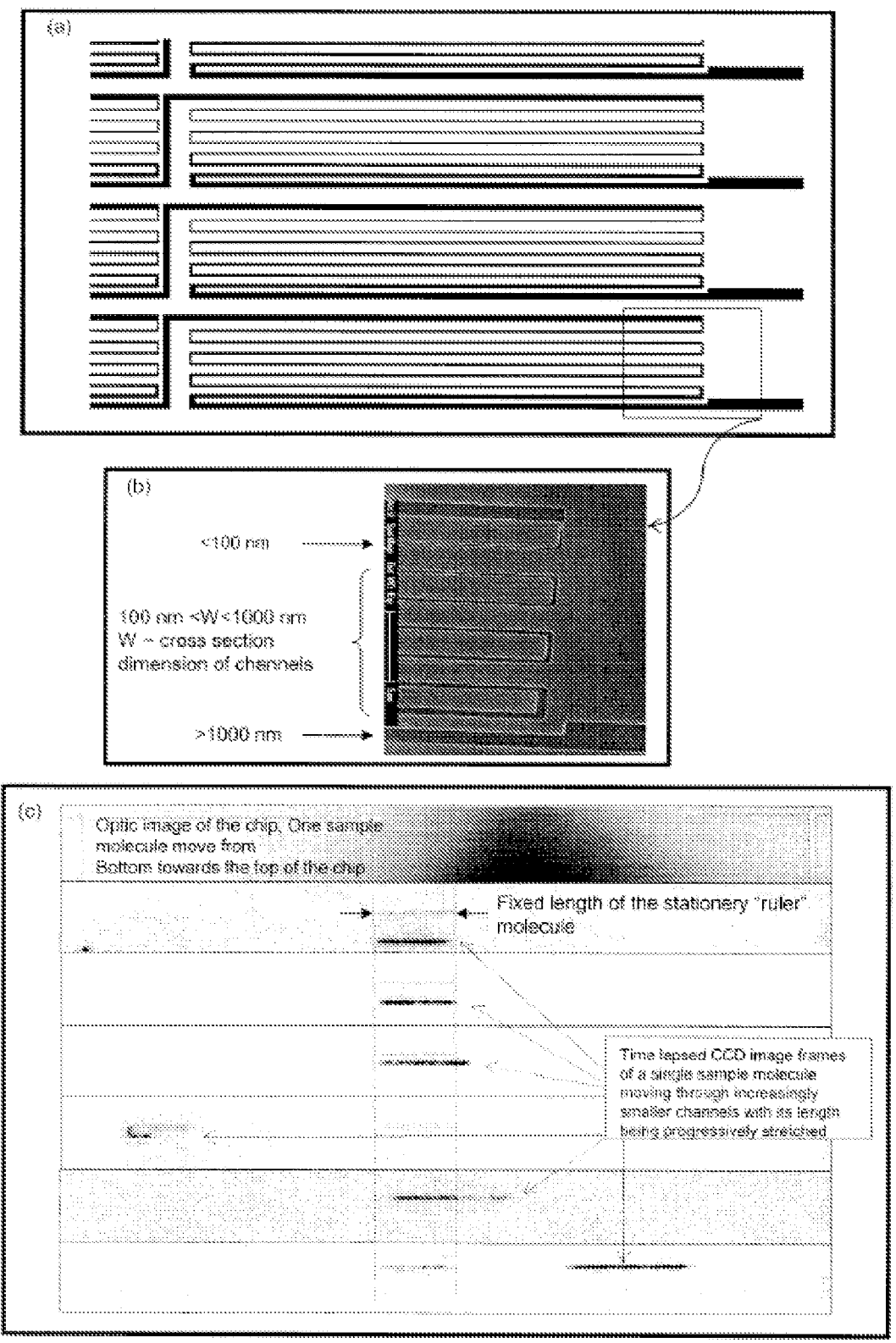
FIG. 11 depicts multiple, long nanochannels arranged in a continuously connected serial set of parallel nanochannels.
Figure 12:
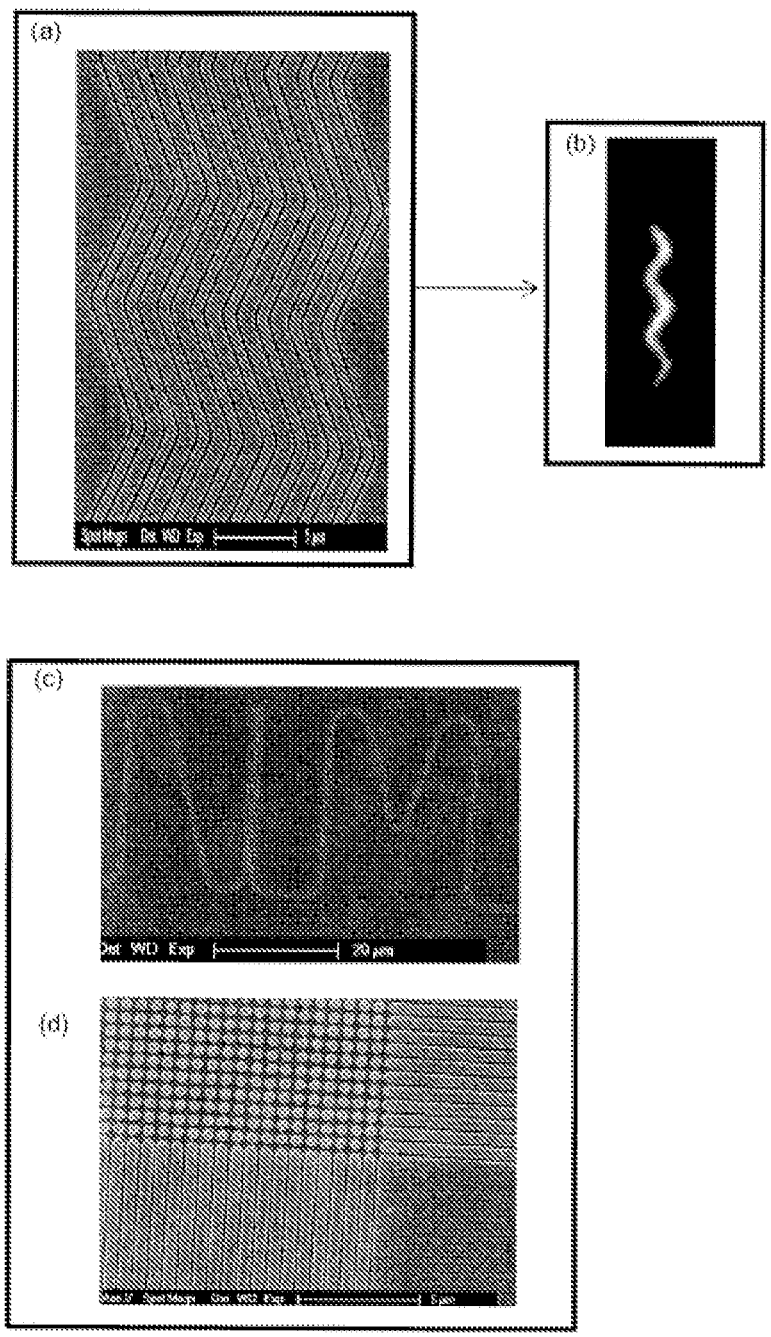
FIG. 12 illustrates various, non-limiting embodiments of channel devices according to the claimed invention.

In some configurations, the nanochannel has at least one linear segment having a length in the range of from about 0.1 microns to about 50 microns. Linear segments are shown in FIG. 10, FIG. 11, and FIG. 12. The nanochannel may include a bend or curve of at least about 30 degrees, at least about 90 degrees, or even a bend of about 180 degrees or more. In some embodiments, a nanochannel is circular or can even be in a spiral configuration.

A nanochannel may possess a constant width and depth, but may also have width that varies, a depth that varies, or both. Channels may be zig-zag in form (FIG. 12), or may have an undulating floor, giving the channel a varying depth along its length.

In some embodiments, like that shown in FIG. 5(b), the nanochannel analysis region is in fluid communication with a first back-end branched channel region. Back-end branched regions are suitably similar to the previously described front-end branched regions, and can be characterized as being downstream from the front-end branched channel region. The front- and back-end regions on a given device may be the same or differ from one another. The devices may also include a second interconnector channel (FIG. 5(b)) that is in fluid communication with a port (inlet or outlet), with a branched region (FIG. 5(b)), or both. A primary channel may also be in fluid communication with a second interconnector channel, or even with a second (e.g., outlet) port.

In some embodiments, the ratio of a cross-sectional dimension of the port to a cross-sectional dimension of the at least one nanochannel is in the range of from about 1 to about $10^7$. In some cases, the ratio is 100, 1000, or even 10,000. The ratio demonstrates that the claimed devices are suitable for transporting (and also analyzing) a target that is transported from a micro- (or larger) scale environment to a nano-scale environment.

This ability to controllably translocate targets from a macroscale environment to a micro- or nano-scale environment is of great value because it enables a user to begin with a large volume of sample (typically molecules or other targets dispersed in a fluid) and then utilize devices according to the claimed invention to controllably isolate a single targets from that large sample. Moreover, the claimed inventions allow the user to isolate that single target in a nanoscale environment, such as a channel. The claimed invention thus enables a user to perform single-molecule analysis on an individual molecule that is formerly dispersed—with many other molecules—in a large volume of media.

In some embodiments, the nanochannel analysis region and a branched channel region are disposed in the same plane. In others, they are in different planes. The nanochannel analysis region can be is in fluid communication with a second nanochannel analysis region, the second nanochannel analysis region being disposed in a different substrate than the first nanochannel analysis region. In such embodiments, stacked or three-dimensional multi-analysis region devices may be constructed, and meta-devices that include multiple nanochannel analysis regions may be constructed.

Also provided are methods of fabricating analysis devices. These methods include, inter alia, bonding a first substrate and a second substrate, at least one of the substrates including at least one channel having a width in the range of from about 10 nm to about 10,000 nm, the bonding giving rise to an enclosed conduit disposed between the substrates, the enclosed conduit being capable of transporting a fluid therethrough.

Bonding may be accomplished by anodic bonding, thermal bonding, or any combination thereof. Chemical bonding may also be used. Sample process conditions for anodic bonding of a Si-glass device are described elsewhere herein.

The methods can include disposing a thin film atop at least a portion of the first substrate, the second substrate, or both, which thin film may be disposed within at least a portion of any channels disposed in the substrate. The film may be used to enhance bonding between the substrates.

As one non-limiting example, a silicon dioxide (or silicon nitride) film may be used to enhance (or even enable) bonding between a silicon substrate and a glass or other substrate. The thin film may also be chosen so as to electrically insulate at least a portion of the interior of the enclosed conduit from at least one of the substrates. As described elsewhere herein in more detail, a thin film may be used to shield at least a portion of the conduit from a substrate, which can prevent the substrate from quenching a fluorophore disposed within the conduit.

Figure 4:
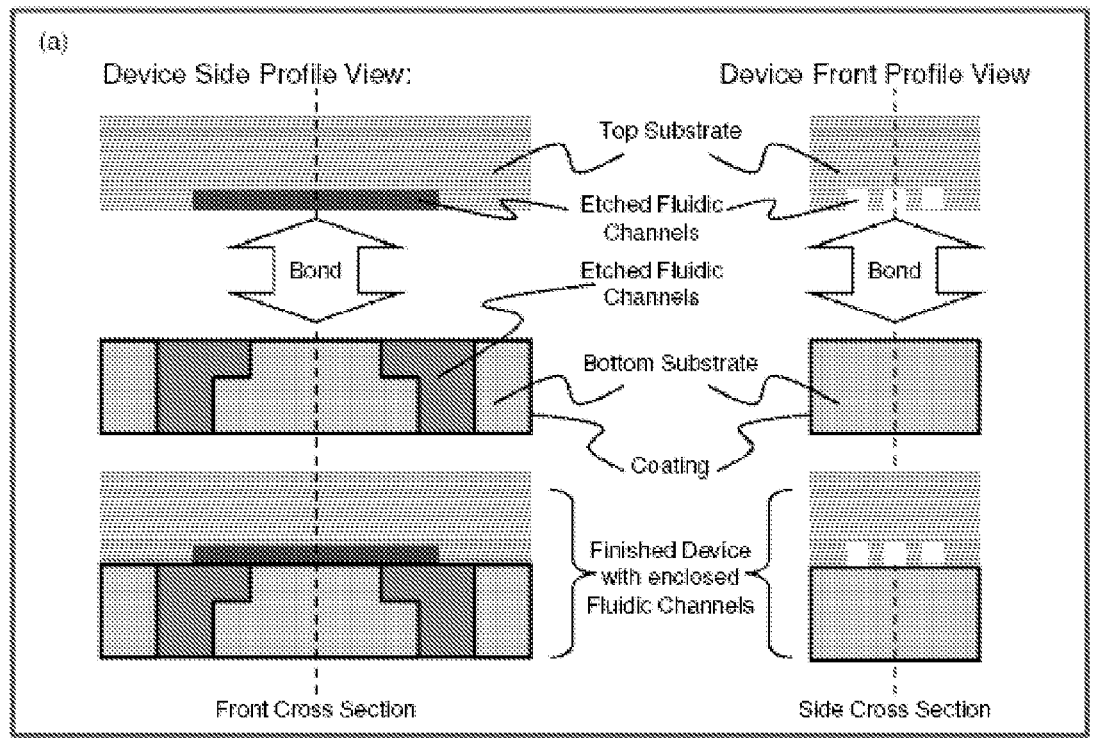
FIG. 4 depicts an example fabrication scheme for two substrates (substrates A and B; one of the substrates suitably being transparent), with channel elements etched into both substrates.
Figure 4:
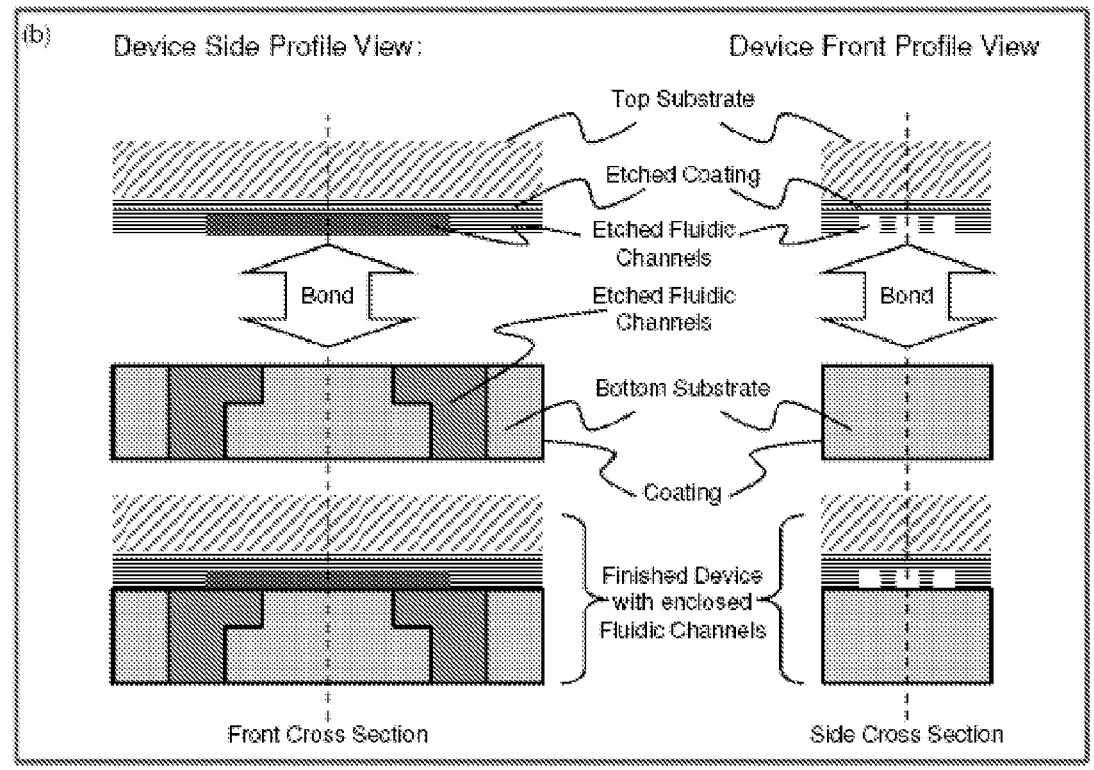

The thin film may be disposed so as to reduce the cross-sectional area of the enclosed conduit to a predetermined value, which reduction is accomplished by building up the floor and sides of a channel so as to reduce the cross-sectional area available to a fluid flowing within the conduit. The thin film may be disposed to reduce the cross-sectional area by at least about 1%, at least about 5%, or even by at least about 10% or even 25%. The thin film can even be disposed to completely fill the channel. Channels can be etched in the film, as shown in, e.g., FIG. 4 and FIG. 16.

A substrate can include two or more channels. Two of the substrates may each include at least one channel such that the bonding gives rise to two or more enclosed conduits disposed between the substrates. In embodiments where both substrates include a channel, the substrates may be bonded so that the channels are in at least partial registration with one another (e.g., FIG. 13).

In some embodiments, the ratio of the widths of two conduits of the resultant device is in the range of from about 1 to about $10^7$, or in the range of from about 100 to about 10,000, or is even about 1000.

In some embodiments, the first substrate, the second substrate, or both, includes a dielectric. The first substrate, the second substrate, or both, can include a semiconducting material, or even a conducting material. One or both of the substrates is suitably transparent to at least one wavelength of electromagnetic radiation, or even transparent to visible light.

Also provided are methods of analysis. The methods suitably include translocating a macromolecule through at least two channels of successively decreasing width such that at least a portion of the macromolecule is elongated while disposed in the narrowest of the channels, the ratio of the widths of the widest and narrowest channels being in the range of from about 1 to about $10^7$, or even from about 100 to about $10^5$. In some embodiments, the macromolecule is translocated through a single channel of decreasing width or cross-sectional area, various widths along the channel being in accordance with the aforementioned ratio.

In some embodiments, the user may translocate a target through an inlet having a cross-sectional dimension in the centimeter range, with the target ultimately arriving at a channel having a cross-sectional dimension in the nanometer range.

The methods also include detecting a signal from the molecule while it resides in a first region of a channel having a width of from 10 nm to about 1000 nm, or from about 50 nm to about 500 nm, or from about 100 nm to about 200 nm.

The user can then correlate the signal to a property of the macromolecule. For example, after exposing the sample to a fluorescent tag that binds to a unique DNA sequence on a sample, the user can then interrogate the sample to determine whether the fluorescent tag is present (or not present) on the sample. The user may also correlate the duration of the signal to the length or other property of the macromolecule, or even the macromolecule's velocity through the device.

The signal need not be emitted by a fluorescent molecule; the signal can be magnetic or radioactive. In some embodiments, the user may optically inspect the target while it is disposed in a channel (or conduit). The signal may be a signal evolved from exciting a label, or it may be a signal or reflection that is effected by illuminating the sample. In embodiments where optical inspection of the sample may be performed, or where the signal includes electromagnetic radiation, it is desirable—though not necessary—for at least one of the substrates (and any intervening thin films) to be transparent.

Translocation may be accomplished by application of an electrical gradient, a pressure gradient, a magnetic field, a thermal gradient, or any combination thereof. The translocation may include applying a constant gradient, or a varying gradient.

The methods further include translocating the macromolecule through at least two channels of successively increasing width. In some embodiments, the direction of the gradient may be reversed so as to reverse the direction of the macromolecule such that at least a portion of the macromolecule re-enters the first region of the channel. The user can thus move a target macromolecule back and forth within a given device.

This back-and-forth control, akin to advancing and rewinding a tape in a tape player, is useful in analyzing a macromolecule or other target because the user may pass the target through the nanochannel analysis region and then "rewind" the macromolecule by reversing the gradient, and then re-analyze the same molecule. This enables the user to easily repeat measurements of a given target, allowing the user to quickly assemble a large (i.e., statistically useful) set of measurements. The ability to adjust the gradient also allows a user to quickly advance (or "fast forward") a target through one portion of the analysis device, and then slow the target down for analysis.

Detection is suitably accomplished optically, electrically, magnetically, electromagnetically, or combinations thereof. Photon counters and microscopes are suitable for performing detection according to the claimed methods.

In another aspect, the present invention provides analysis devices. These devices suitably include a first substrate and a second substrate, the first and second substrates defining a channel disposed between the substrates, at least one of the first or second substrates permitting at least partial passage of electromagnetic radiation characterized as having at least one wavelength in the range of from about 10 nm to about 2500 nm; a first thin film surmounting at least a portion of the first substrate, the second substrate, or both.

The thin film can be a single layer of material. A substrate may be surmounted by multiple films, and a thin film may itself be composed of a single material or a combination of materials. A substrate may be surmounted by one, two, three, or more discrete thin films. In some embodiments, the substrate or thin film may act as a waveguide or illumination source, so as to enhance observation of a target disposed within the device.

At least a portion of the first thin film suitably defines at least a portion of a channel disposed between the first and second substrates, the first thin film giving rise to a reduced background signal of the device when the device is illuminated by electromagnetic radiation having a wavelength in the range of from about 10 nm to about 2500 nm, relative to an identical device without said first thin film.

The thin film is suitably bonded to the first substrate, the second substrate, or both. The substrates are suitably bonded to one another, and the bonding may be through the thin film or thin films. In some embodiments, a thin film is bonded to a substrate. Thin films may, in some embodiments, be bonded to one another.

The first thin film suitably includes silicon nitride. The first thin film may also include, e.g., silicon oxynitride, $SiO_xN_y$, hydrogenated silicon dioxide, hydrogenated silicon nitride, hydrogenated silicon oxynitride, high K dielectrics, compounds including titanium: TiSiO, TiO, TiN, titanium oxides, hydrogenated titanium oxides, titanium nitrides, hydrogenated titanium nitrides, TaO, TaSiO, TaOxNy, $Ta_2O_5$, TaCN, tantalum oxides, hydrogenated tantalum oxides, tantalum nitrides, hydrogenated tantalum nitrides.

Compounds that include hafnium are also suitable, and include $HfO_2$, $HfSiO_2$, $HfZrO_x$, HfN, HfON, HfSiN, HfSiON, hafnium oxides, hydrogenated hafnium oxides, hafnium nitrides, hydrogenated hafnium nitrides, $ZrO_2$, $ZrSiO_2$, ZrN, ZrSiN, ZrON, ZrSiON, zirconium oxides, hydrogenated zirconium oxides, zirconium nitrides, hydrogenated zirconium nitrides, $Al_2O_3$, AlN, TiAlN, TaAlN, WAlN, aluminum oxides, hydrogenated aluminum oxides, aluminum nitrides, hydrogenated aluminum nitrides.

Suitable materials also include WN, low K dielectrics, fluorine doped silicon dioxide, carbon doped silicon dioxide, porous silicon dioxide, porous carbon doped silicon dioxide, spin-on organic polymeric dielectrics, graphite, graphene, carbon nano-tubes, plastics, polymer, organic molecules, self-assembled monolayers, self-assembled multi-layers, a lipid bi-layer, any of the aforementioned compounds in an hydrogenated form, a stoichiometric variation of any of the foregoing, and combinations thereof.

The first substrate, the second substrate, or both, may include glass, silicon, or a combination of the two. In some embodiments, one or both of the substrates includes quartz, fused silica, sapphire, silicon carbide, soda lime, germanium, silicon germanium, gallium, indium, cadmium, zinc, aluminum, stainless steel, Kapton™ polymeric material, a polymer, a semiconductor material, a metal, a ceramic, and the like. The substrates may also include combinations of these materials.

At least one of the substrates is suitably transparent to at least one frequency of electromagnetic radiation. In some embodiments, one or both of the substrates is essentially transparent to visible light. This transparency facilitates the observation of targets (e.g., fluorescently labeled macromolecules) that may be disposed within the devices.

Suitable glasses include Schott Borofloat™ 33 glass, Pyrex 7740™ glass, Hoya SD2™ glass, combinations thereof, and the like.

Substrates suitably have a thickness in the range of from about 0.01 mm to about 5 mm, or from about 0.1 mm to about 1 mm, or even about 0.5 mm.

The first thin film may have a thickness in the range of from about 1 nm to about 5000 nm, or from about 10 nm to about 1000 nm, or from about 50 nm to about 500 nm, or even from about 100 nm to about 200 nm.

The conduits of the claimed devices suitably have a width in the range of from about from about 5 nm to about 5 mm, or from about 10 nm to about 1 mm, or from 50 nm to about 1 micron, or from about 100 nm to about 500 nm. The channels suitably have a depth in the range of from about 5 nm to about 1 mm, or from about 100 nm to about 1000 nm.

The devices may also include a second thin film. The second thin film is suitably chosen so as to give rise to a reduced background signal of the device when the device is illuminated by electromagnetic radiation having a wavelength in the range of from about 10 nm to about 2500 nm, relative to an identical device without said second thin film. Silicon nitride is considered especially suitable for use as a thin film.

Other materials may also be used in the second thin film. These materials include, inter alia, silicon oxynitride, SiOxNy, hydrogenated silicon dioxide, hydrogenated silicon nitride, hydrogenated silicon oxinitride, high K dielectrics, compounds including titanium: TiSiO, TiO, TiN, titanium oxides, hydrogenatedtitanium oxides, titanium nitrides, hydrogenated titanium nitrides, TaO, TaSiO, TaOxNy, $Ta_2O_5$, TaCN, tantalum oxides, hydrogenated tantalum oxides, tantalum nitrides, hydrogenated tantalum nitrides, compounds containing hafnium: HfO2, $HfSiO_2$, HfZrOx, HfN, HfON, HfSiN, HfSiON, hafnium oxides, hydrogenated hafnium oxides, hafnium nitrides, hydrogenated hafnium nitrides, $ZrO_2$, $ZrSiO_2$, ZrN, ZrSiN, ZrON, ZrSiON, zirconium oxides, hydrogenated zirconium oxides, zirconium nitrides, hydrogenated zirconium nitrides, $Al_2O_3$, AlN, TiAlN, TaAlN, WAlN, aluminum oxides, hydrogenated aluminum oxides, aluminum nitrides, hydrogenated aluminum nitrides, SiN, WN, low K dielectrics, fluorine doped silicon dioxide, carbon doped silicon dioxide, porous silicon dioxide, porous carbon doped silicon dioxide, spin-on organic polymeric dielectrics, graphite, graphene, carbon nano-tubes, plastics, polymer, organic molecules, self-assembled monolayers, self-assembled multi-layers, a lipid bi-layer, any of the aforementioned compounds in an hydrogenated form, a stoichiometric variation of any of the foregoing, combinations thereof, and the like.

The second thin film suitably has a thickness in the range of from about 1 nm to about 5000 nm, or from about 100 nm to about 1000 nm, or even from about 300 nm to about 500 nm. A thin film may be selected so as to prevent or reduce quenching of a fluorescent molecule disposed within the device by exposure to the first substrate, second substrate, or both. A thin film may also be selected so as to reduce the background signal evolved from the device.

The present invention also provides analysis devices. These devices suitably include a substrate configured so as to define a channel enclosed within the substrate, and the substrate being transparent to electromagnetic radiation having at least one frequency component in the range of from about 10 nm to about 2500 nm.

The channel is suitably characterized as being a conduit, although other configurations are within the scope of the invention. The channel also suitably has at least one cross-sectional dimension (e.g., width, diameter) in the range of from about 5 nm to about 5 mm, or in the range of from about 50 nm to about 500 nm, or even about 75 nm to about 100 nm. The channel is suitably formed in silicon nitride, although other materials that are essentially transparent to at least one wavelength of electromagnetic radiation may be used.

Figure 19:
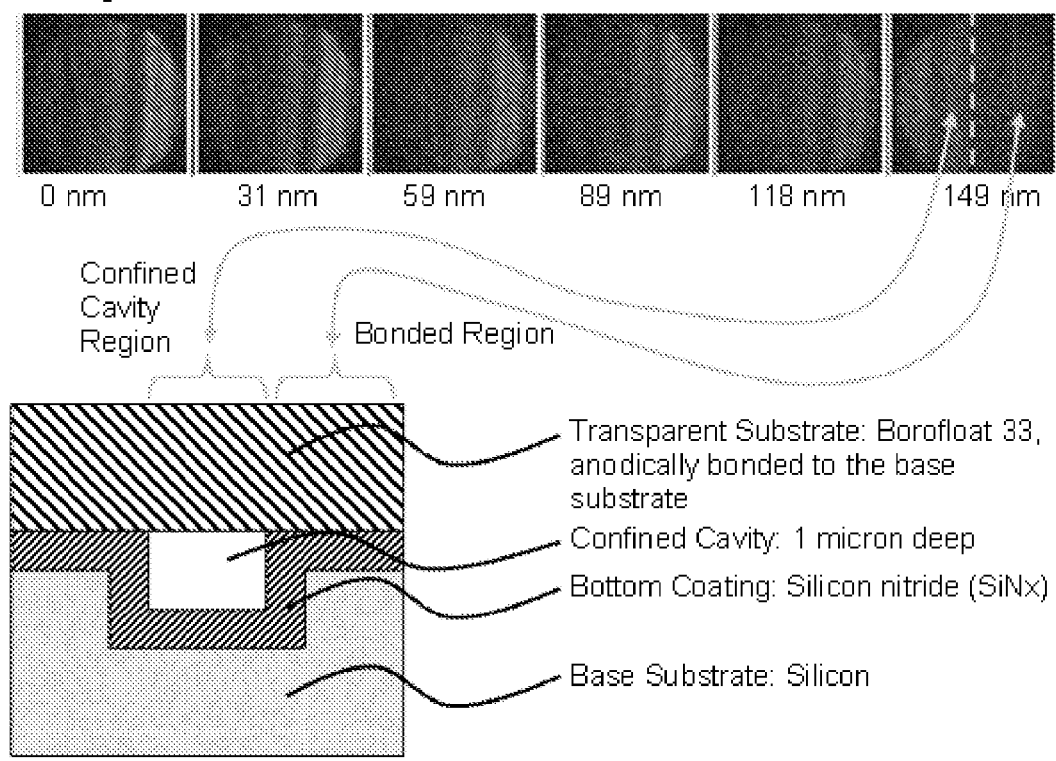
FIG. 19 illustrates background measurements taken at radiation wavelengths of from about 0 nm to about 217 nm of confined channels having a $SiN_x$ thin film disposed at the bottom of the channel.

Silicon nitride is considered especially suitable because, as described elsewhere herein, the material is sufficiently transparent to visible light (and other wavelengths) to facilitate observation of a sample disposed within. Further, silicon nitride—as shown in FIG. 19—does not effect quenching of flurophores disposed nearby, which further facilitates analysis of labeled targets disposed within the devices.

Also provided are methods of fabricating analysis devices. These methods include, inter alia, disposing a first substrate, a second substrate, and a first thin film layer so as to define a channel disposed between the first and second substrates.

The first layer is suitably selected such that the layer reduces the background signal of the device when the device is illuminated by electromagnetic radiation having a wavelength in the range of from about 10 nm to about 2500 nm, relative to an identical device without the thin film. The first thin film layer is suitably bonded to the first substrate, the second substrate, or both.

Some substrates (e.g., quartz to quartz) may be bonded directly to one another. In some embodiments, the substrates are bonded to one another through a thin film; a thin film may be bonded to one or more substrates, and may even be bonded to another thin film. As described elsewhere, a thin film (e.g., an oxide) can enhance (or even enable) bonding between two substrates.

A second thin film layer may be bonded to the first substrate, the second substrate, the first thin film layer, or combinations thereof. Bonding may be anodic, thermal, chemical, or by other methods known to those of skill in the art.

The first thin film layer (or other thin film layers) are suitably selected such that the thin film layer reduces (or otherwise minimizes) quenching of fluorophores disposed within the device. Without being bound to any particular theory, the thin film may act as a shield between the fluorophore and one or more of the device's substrates.

In some embodiments, the thin film serves to provide physical separation between the fluorophore and the substrate; without the thin film, the fluorophore would reside relatively close to the substrate material, and the fluorophore's may be reduced or otherwise quenched by the substrate material as the fluorphore resides in a channel that acts as a "dark well." Silicon nitride is considered a suitable material for reducing quenching.

Also provided are methods of fabricating analysis devices. These methods include disposing a sacrificial material or template within a workpiece including a material that is transparent to electromagnetic radiation having a wavelength in the range of from about 10 nm to about 5000 nm. The user then removes at least a portion of the sacrificial template so as to give rise to a channel disposed within the workpiece, and at least a portion of the channel having a cross-sectional dimension in the range of from about 5 nm to about 5000 nm.

In one embodiment, a tube, cord, or other sacrificial material is embedded in the radiation-transparent material; this may be accomplished by lithographic processes, by softening the radiation-transparent material, or by other methods. The sacrificial material is then removed—by heating, etching, vaporizing, or other process—so as to leave behind a channel in the radiation-transparent substrate. Controlling the dimensions and orientation of the sacrificial material thus enables the user to achieve channels of various size and geometry.

The channels suitably have at least one cross-sectional dimension (e.g., diameter, width, or even depth) in the range of from about 5 nm to about 5000 nm, or from about 10 nm to about 1000 nm, or from about 50 nm to about 500 nm. The channel may have a constant cross-section or a varying cross-section. A given device may include two or more channels, which channels may be in fluid communication with one another.

Also provided are methods of analyzing fluorescently labeled molecules. The methods include placing at least a portion of the fluorescently labeled molecule into a channel within an analysis device, the device suitably having at least a first substrate, a second substrate, and a first thin film configured to give rise to the channel being disposed between the first and second substrates.

The devices suitably include a first thin film bonded to the first substrate, the second substrate, or both. The fluorescently labeled molecule is suitably capable of emitting electromagnetic radiation of an emission wavelength when the sample is illuminated by electromagnetic radiation of an excitation wavelength in the range of from about 10 nm to about 2500 nm, and the first thin film suitably reduces the background signal of the device when the device is illuminated by electromagnetic radiation of the excitation wavelength, relative to an identical device without said first thin film. The user then collects electromagnetic radiation of the emission wavelength emitted from the fluorescently labeled molecule.

The background signal of the device is attributable to the first substrate, the second substrate, or both. The addition of a thin film can, in some embodiments, increase the background signal of the device (e.g., silicon dioxide).

Figure 13:
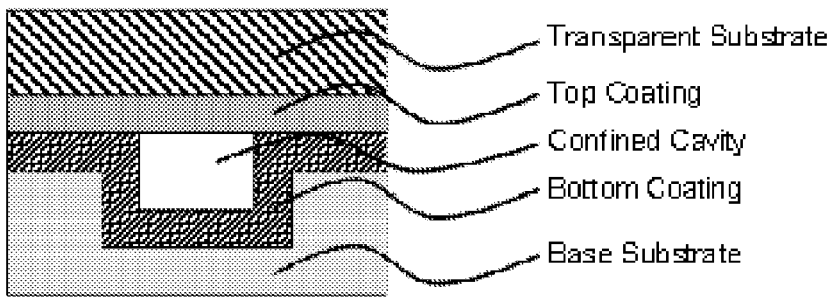
FIG. 13 depicts cross-sectional views of devices according to the claimed invention, with (a) a channel formed in the lower substrate, (b) channels formed in both the lower and upper substrates, and (c) a channel formed in the upper substrate only—each of these three embodiments depicts upper and lower thin films.
Figure 13:
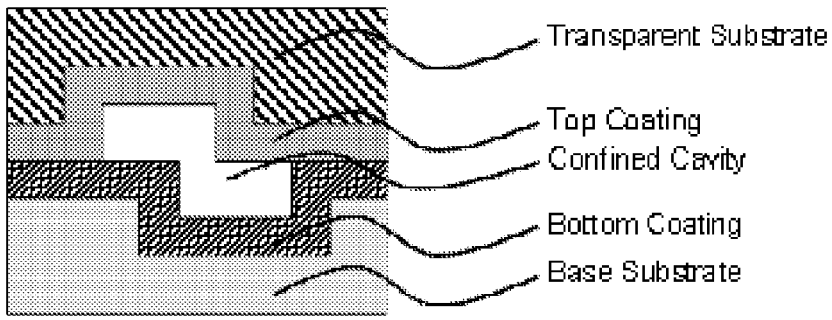
Figure 13:
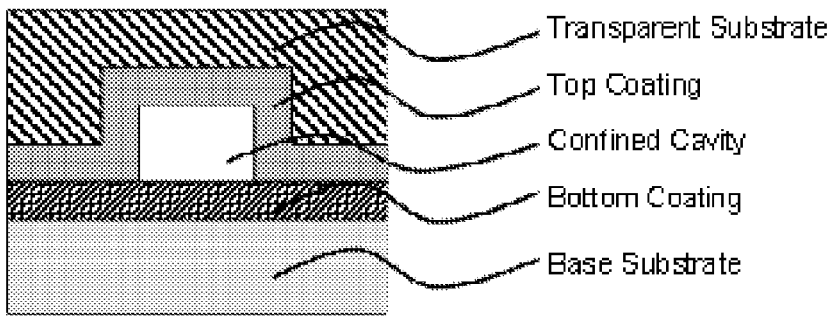

Devices according to the claimed invention may include two substrates, with one or more channels etched into the base substrate, the transparent substrate, or both, as shown in non-limiting FIG. 13. As shown in that figure, the base substrate is given a "bottom thin film" before bonding to reduce the background, and the transparent substrate (in some embodiments) can also be given a "top thin film".

The bottom and top thin films suitably conform to the transparent and base substrates, also as shown in FIGS. 13(*a*), (*b*), and (*c*). One or more of the thin films is suitably bound to one or more of the substrates. In some embodiments, thin films may be bonded to one another, and substrates may also be bonded to one another. In some embodiments, channels are formed in facing substrates, coatings, or both, and the channels may be placed in registration with one another so as to give rise to a "combined" channel that is defined by two channels (FIG. 13(b), FIG. 14(b), FIG. 15(b), and FIG. 16(b), for example) placed into registration with one another.

A substrate, or a thin film, may have channels, pillars, ramps, bumps, or even notches formed thereon. In some embodiments, substrates bonded to each other each have different features patterned and etched thereon such that bonding the substrates to one another results in a device having a combination of the substrates' features. As one non-limiting example, an upper substrate may be etched with a set of comparatively wide channels, and a lower substrate may be patterned with an array of micropillars, positioned such that when the substrates are bonded together, the pillars of the lower substrate are disposed within the channels of the upper substrate. Such a device might be similar to the devices shown in FIG. 9.

In some embodiments, one or more valves are used to modulate fluid flow within a device. As one example, a valve may be disposed at the inlet or outlet of a device.

Figure 14:
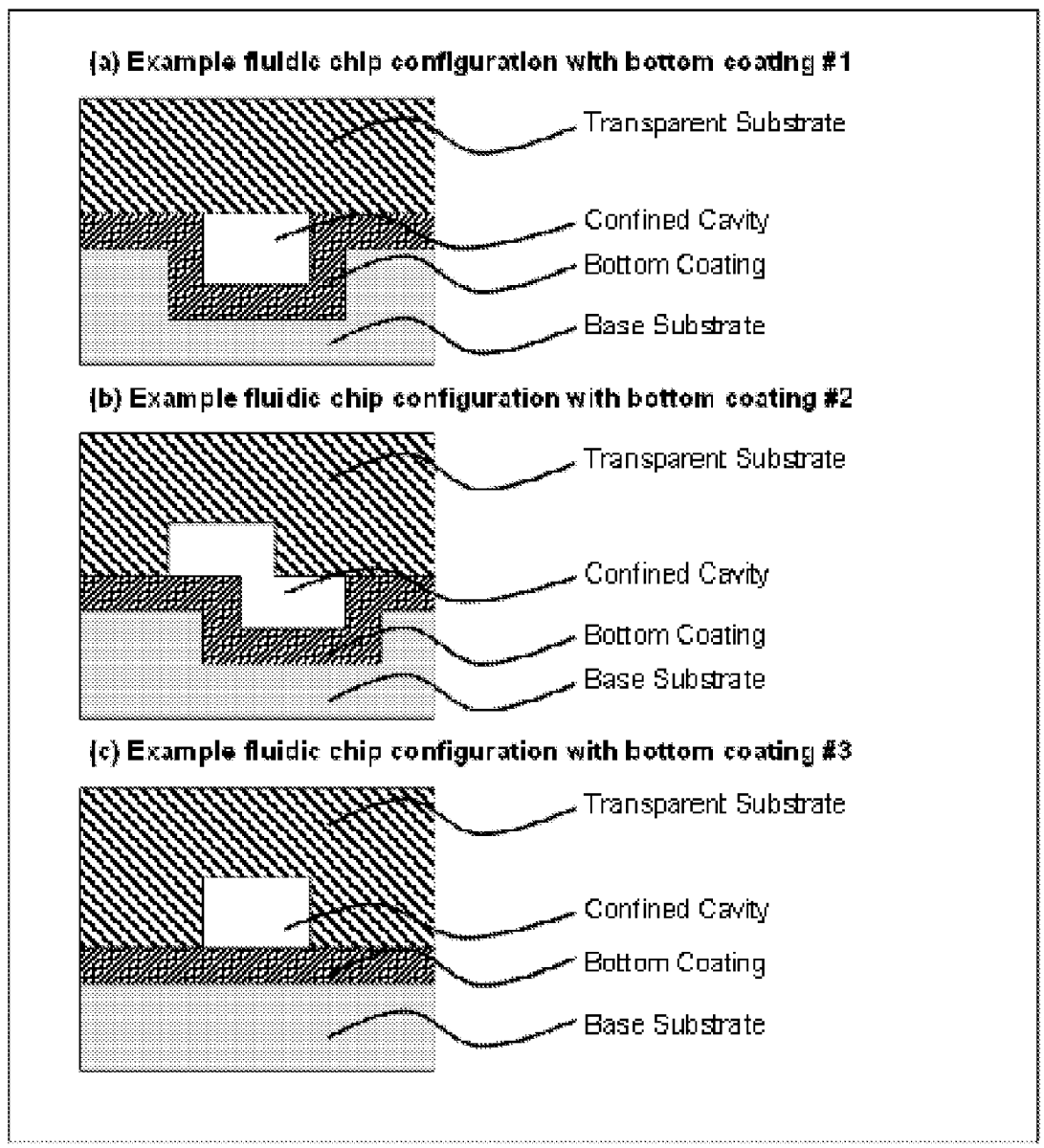
FIG. 14 depicts cross-sectional views of devices according to the claimed invention, with (a) a channel formed in the lower substrate, (b) channels formed in the upper and lower substrates, and (c) a channel formed in the upper substrate only—each of these embodiments depicts only a single thin film that conforms primarily to the lower substrate.
Figure 15:
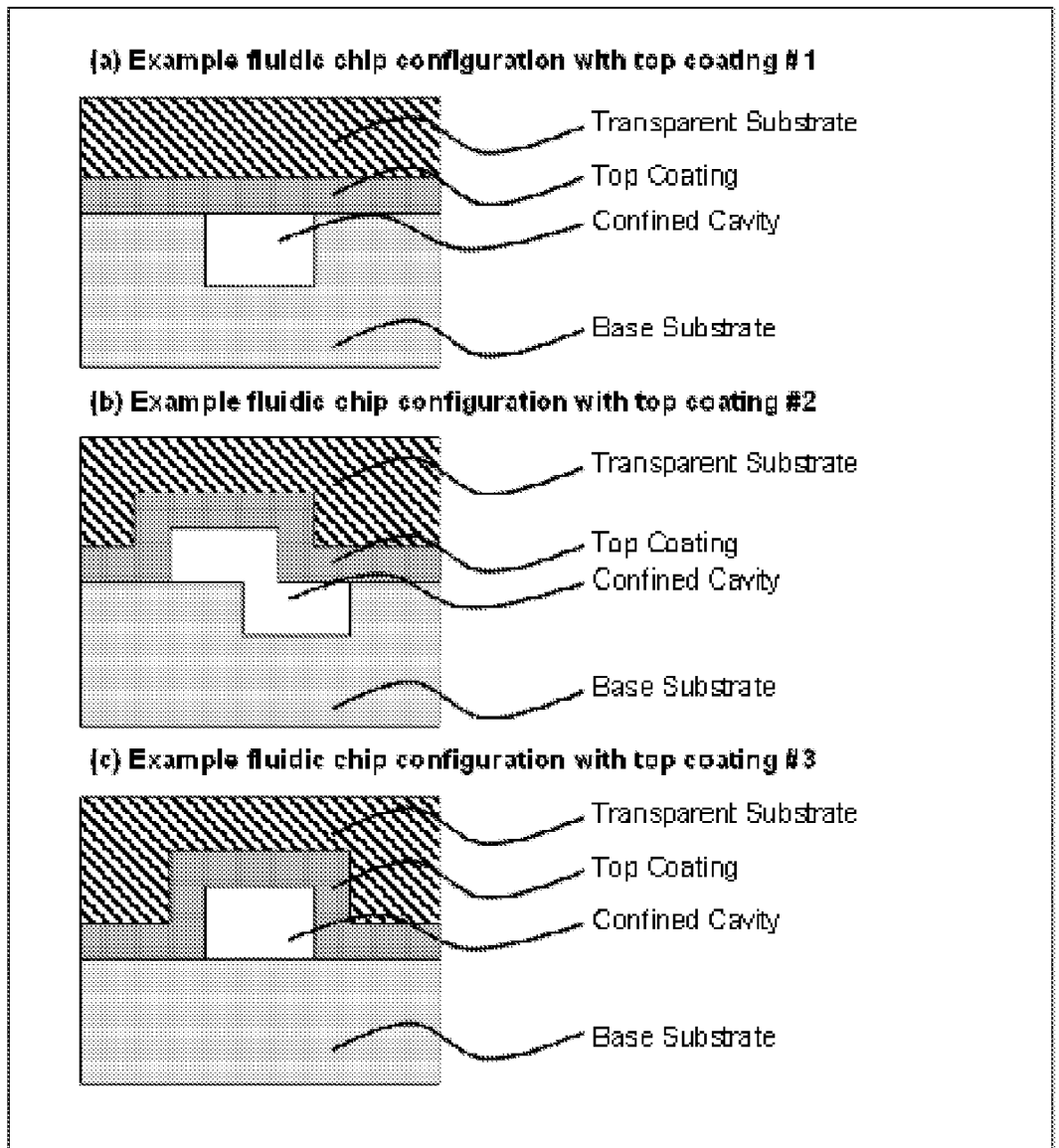
FIG. 15 depicts cross-sectional views of devices according to the claimed invention, with (a) a channel formed in the lower substrate, (b) channels formed in the upper and lower substrates, and (c) a channel formed in the upper substrate only—each of these embodiments depicts only a single thin film that conforms primarily to the upper substrate.

FIG. 14 and FIG. 15 depict devices having two substrates and only a single thin film layer. The single thin film layer suitably conforms to at least one of the substrates, as shown in FIG. 14 (bottom thin film on base/lower substrate) and FIG. 15 (top thin film on upper, transparent substrate). There may also (not shown) be embodiments having a single substrate and a single thin film, the channel being defined by only that single substrate and that single thin film.

Figure 16:
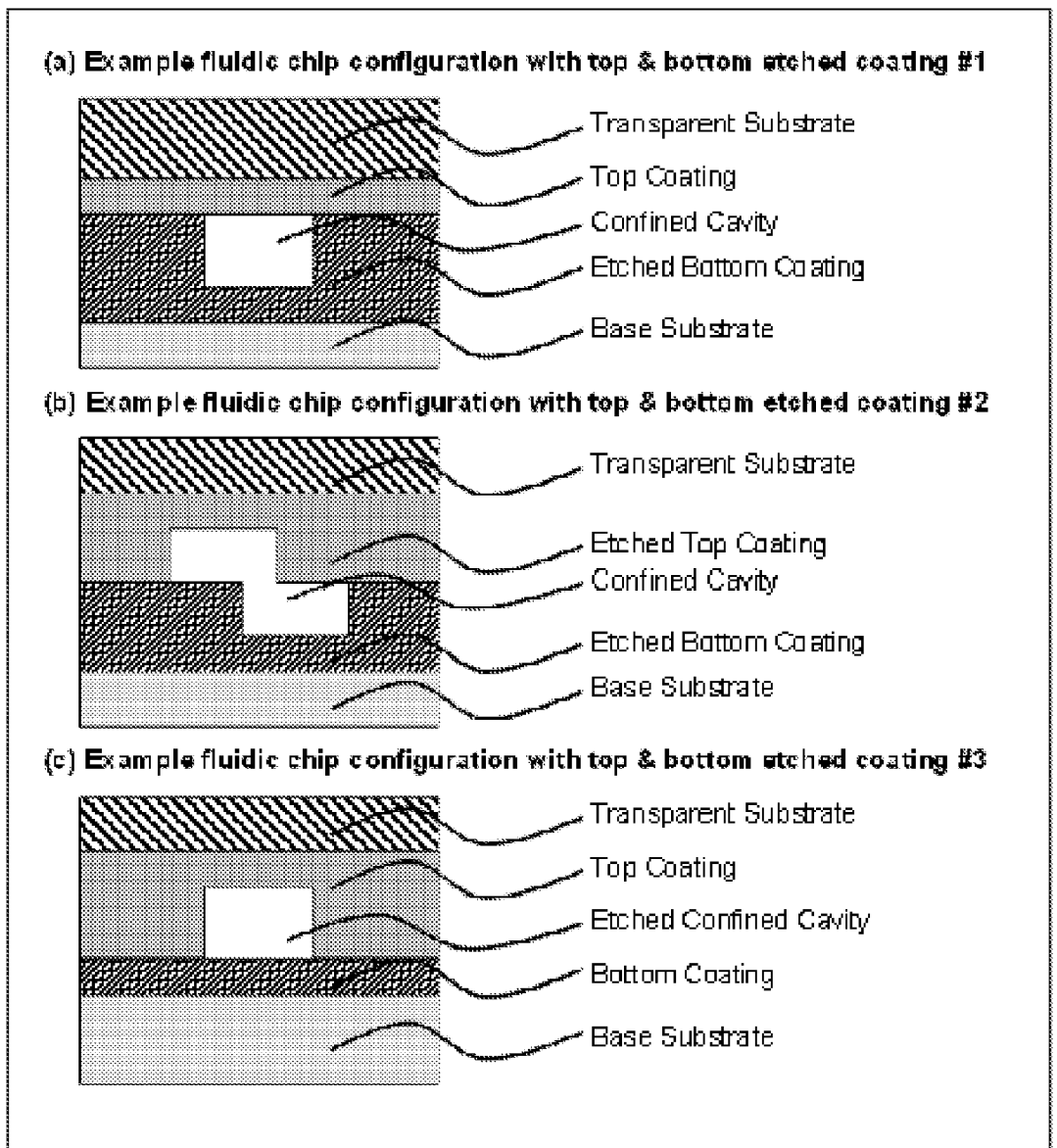
FIG. 16 depicts cross-sectional views of devices according to the claimed invention, with (a) a channel formed in the lower of two thin films, (b) channels formed in the upper and lower thin films, and (c) a channel formed in the upper thin film only.
Figure 17:
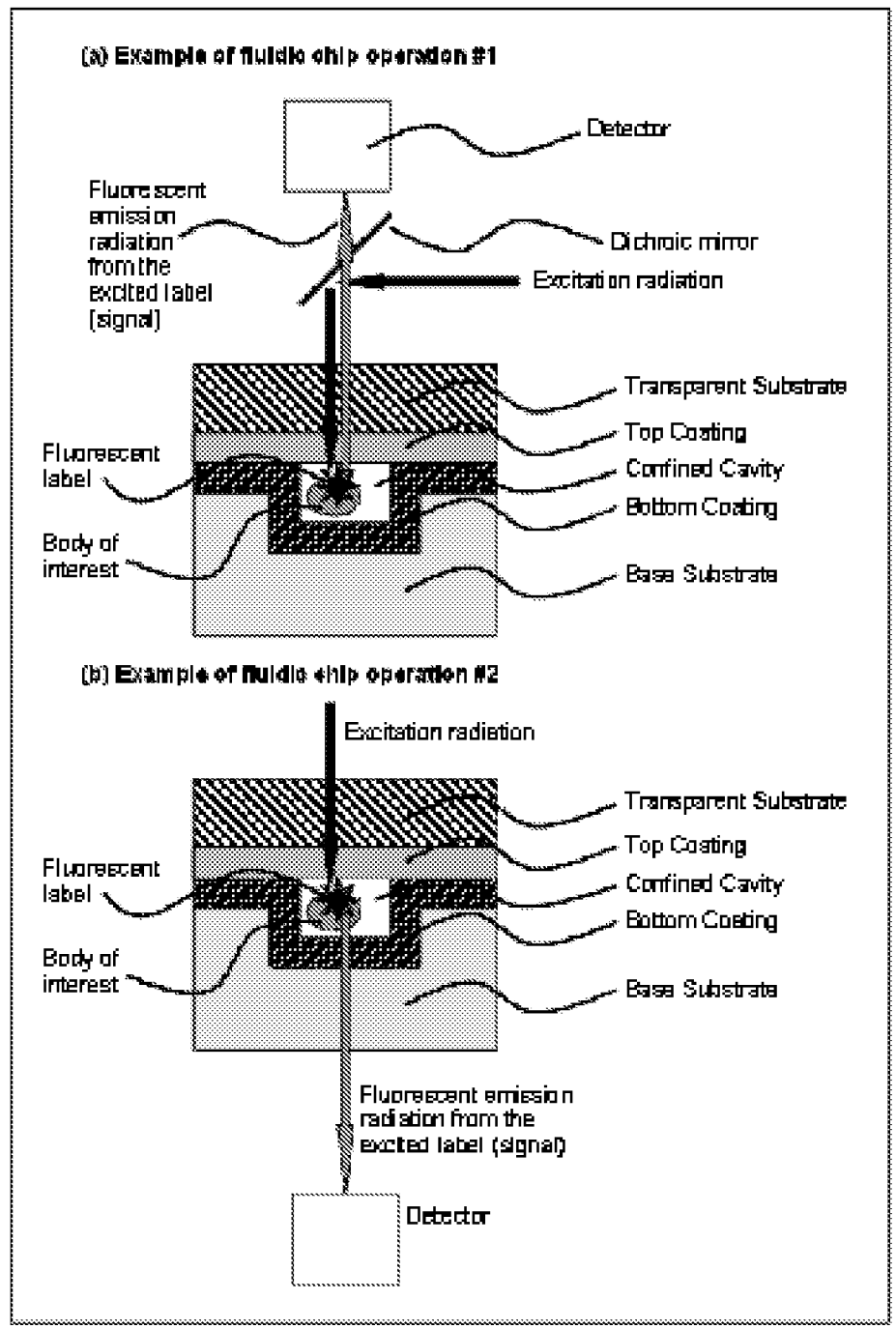
FIG. 17 depicts the operation of a device according to the claimed invention, showing in (a) the excitation of a fluorescently labeled sample disposed in a device made according to the claimed invention and the collection of radiation emitted from the excited sample transmitted across the same substrate and thin film layer across which the excitation radiation passed, and in (b) the excitation of a fluorescently labeled sample disposed in a device made according to the claimed invention and the collection of radiation emitted from the excited sample transmitted across a different substrate and thin film layer than those across which the excitation radiation passed.

FIG. 16 and FIG. 17 illustrate additional embodiments. As shown in those figures, a channel may be formed in a thin film (as contrasted with in a substrate, as shown in FIG. 13, FIG. 14, and FIG. 15). In these further configurations, planar substrates may be used, and the thin film may be disposed (e.g., deposited, grown, etc.) so as to give rise to a trench, slot, or other channel. Alternatively, the thin film may be disposed, followed by removal of part of the thin film (e.g., by etching, ablation, or by other techniques) so as to give rise to a channel of the desired dimensions and orientation.

In other embodiments (FIG. 14(b)), channels may be formed in both a substrate and a thin film layer, depending on the user's needs. The channels or channels may be formed in a thin film on the upper or lower substrate.

The confined channel suitably contains, during operation, a medium in which labeled bodies of interest (e.g., FIG. 17). Suitably, the labeled bodies include fluorophores that are fluorescently excited in the channels by passing electromagnetic radiation through a transparent substrate (and, in some embodiments, a thin film), with the excited labels then emitting an electromagnetic radiation signal back through a transparent substrate, where the emission is then detected (FIG. 17(a)).

Other potential embodiments include those configurations that use multiple energy transfer steps (such as fluorescence resonance energy transfer, "FRET") before the electromagnetic radiation signal is emitted from the confined channel, through the transparent substrate. FIG. 17 is exemplary only, and other detection schemes may be used in connection with the claimed invention; FIG. 17(b) shows an embodiment where the base substrate is transparent to the wavelength of the signal's electromagnetic radiation. The user may also detect a magnetic, radioactive, or electrical signal.

Transparent Layer

The transparent substrate (e.g., the upper substrate in FIG. 13) is suitably a material capable of being permanently bonded to the base substrate, or is transparent to the electromagnetic radiation in the frequency of interest, or both.

Suitable substrate material is a glass or other material that permits at least partial passage of visible light, while also having similar thermal expansion characteristics to that of the base substrate in the temperature range of about 0° C. to about $T_b$, where $T_b$ is the bonding temperature. The glass may suitably be Schott Borofloat 33™, Pyrex 7740™, or Hoya SD2™, and base substrate silicon.

Other suitable substrates include quartz, fused silica, glass, fused quartz, sapphire, silicon carbide, and soda lime glass. The substrate thickness is suitably between between 0.01 mm to 5 mm, or even between 0.01 and 0.3 mm. The substrate may be of uniform thickness or of varying thickness.

The device can be in the form of a chip, slide, or other insertable form. The devices may be inserted into a reader/detector device, or the device may be incorporated into a reader/detector device. The device may include one or more chambers or channels for performing analysis, which analysis may be performed on multiple samples in parallel.

The bonding process is suitably any process that can permanently bond the transparent and base substrates, such as anodic bonding. Other bonding processes include, but are not limited to: fusion, thermal, direct, plasma-activated, chemically-activated, dielectric polymer, and adhesive bonding schemes.

Bottom Thin Film

The bottom thin film (e.g., shown in FIG. 13) is suitably of a different composition from the base substrate, and acts to reduce the background signal of the channel and the surrounding region. This thin film material can be applied by growth, deposition, evaporation, sputtering, spin-thin film, lamination, or plating onto the base substrate. The material can be applied after the etching of the channels or other fluidic elements, or before channels or other structures are etched, in which case the channels or other structures (e.g., fluidic elements) are etched into the thin film, as shown in FIG. 16).

The material can be thermally grown if it is silicon dioxide, or deposited by a low-pressure chemical vapor deposition (LPCVD) or atomic layer deposition (ALD) process, where the material is silicon nitride.

A variety of deposition/application methods may be used for the bottom thin film, including: Physical vapor deposition (PVD), chemical vapor deposition (CVD), plasma enhanced chemical vapor deposition (PECVD), atmosphere pressure CVD (APCVD), ultrahigh vacuum CVD (UHVCVD), aerosol assisted CVD (SSCVD), Direct liquid injection CVD (DLICVD), microwave plasma assisted CVD (MPCVD), atomic layer deposition (ALD), atomic layer CVD, epitaxy, molecular beam epitaxy (MBE), metalorganic vapor phase epitaxy (MOVPE), organometallic vapor phase epitaxy (OMVPE), metalorganic chemical vapor deposition (MOVCD), organometallic chemical vapor deposition (OMCVD), Vapor phase epitaxy (VPE), plating, evaporation, thermal evaporation, electron beam evaporation, pulsed laser deposition, cathodic arc deposition, sputtering, chemical solution deposition, spin thin film, langmuir blodgett film, spray thin film, and the like.

The bottom thin film material thickness can vary from about 1 nm to about 5000 nm, or from about 500 nm to about 1000 nm. The thickness need not be uniform, and is suitably between about 20 and about 500 nm. As shown in the attached figures, the thin film may conform to the surface profile of the substrate that the thin film contacts.

The thin film material is suitably a material that is at least partly electrically insulating. The material selection can be silicon nitride ($SiN_x$ or $Si_3N_4$). Other possibilities include, but are not limited to: dielectrics, ceramics, silicon dioxide ($SiO_2$), silicon oxide, glass, quartz, fused silica, $SiO_x$, silicon oxinitride, $SiN_xO_y$, hydrogenated silicon dioxide, hydrogenated silicon nitride, hydrogenated silicon oxinitride.

High K dielectrics and compounds containing titanium (TiSiO, TiO, TiN, iitanium oxides, hydrogenated titanium oxides, titanium nitrides, hydrogenated titanium nitrides) are also suitable. Similarly, compounds containing tantalum: TaO, TaSiO, $TaO_xN_y$, $Ta_2O_5$, TaCN, tantalum oxides, hydrogenated tantalum oxides, tantalum nitrides, hydrogenated tantalum nitrides are suitable.

Hafnium compounds, such as $HfO_2$, $HfSiO_2$, $HfZrO_x$, HfN, HfON, HfSiN, HfSiON, hafnium oxides, hydrogenated hafnium oxides, hafnium nitrides, hydrogenated hafnium nitrides, zirconium compounds ($ZrO_2$, $ZrSiO_2$, ZrN, ZrSiN, ZrON, ZrSiON, zirconium oxides, hydrogenated zirconium oxides, zirconium nitrides, hydrogenated zirconium nitrides are also suitable. Aluminum compounds, including $Al_2O_3$, AlN, TiAlN, TaAlN, WAlN, aluminum oxides, hydrogenated aluminum oxides, aluminum nitrides, and hydrogenated aluminum nitrides are useful.

SiN, WN, Low-K dielectrics, fluorine doped silicon dioxide, carbon doped silicon dioxide, porous silicon dioxide, and porous carbon doped silicon dioxide are also suitable. Some embodiments may include spin-on organic polymeric dielectrics, graphite, graphene, carbon nano-tubes, plastics, polymer, organic molecules, self-assembled monolayers, self-assembled multi-layers, lipid bi-layers, or any of the aforementioned compounds in an hydrogenated form, stoichiometric variations of the above compounds (e.g., $SiO_x$ rather than $SiO_2$; $Ta_xO_y$ instead of $Ta_2O_5$), combinations thereof, and the like.

The bottom thin film material, application, morphology, and topology are suitably chosen such that it reduces the effective background signal of the device relative to the signal evolved from a body of interest disposed within the channel, and suitably also reduces or even minimizes the quenching of fluorescent (or other) labels used to observe the samples being analyzed. With this guideline in mind, those of ordinary skill will encounter little difficulty in selecting the optimal thin film in view of the signal evolved from the channel at the one or more wavelengths being used to evaluate (i.e., excite) the body of interest, and, in some embodiments, to optimize the signal-to-background levels.

Top Thin Film

The top thin film material's composition, application procedure, topology, morphology and thickness range are suitably the same as the bottom thin film, except that the top thin film is applied to the upper transparent substrate instead of the lower substrate, and that it may not necessarily be present in a particular chip embodiment.

The top or upper thin film material, application, morphology, and topology are suitably chosen so as to reduce the effective background signal of the device relative to the signal evolved from a body of interest disposed within the channel, and suitably also reduces or even minimizes the quenching of fluorescent (or other) labels used to observe the samples being analyzed. With this guideline in mind, those of ordinary skill will encounter little difficulty in selecting the optimal thin film in view of the signal evolved from the channel at the one or more wavelengths being used to evaluate (i.e., excite) the body of interest, and, in some embodiments, to optimize the signal-to-background levels.

Confined Channel

Figure 20:
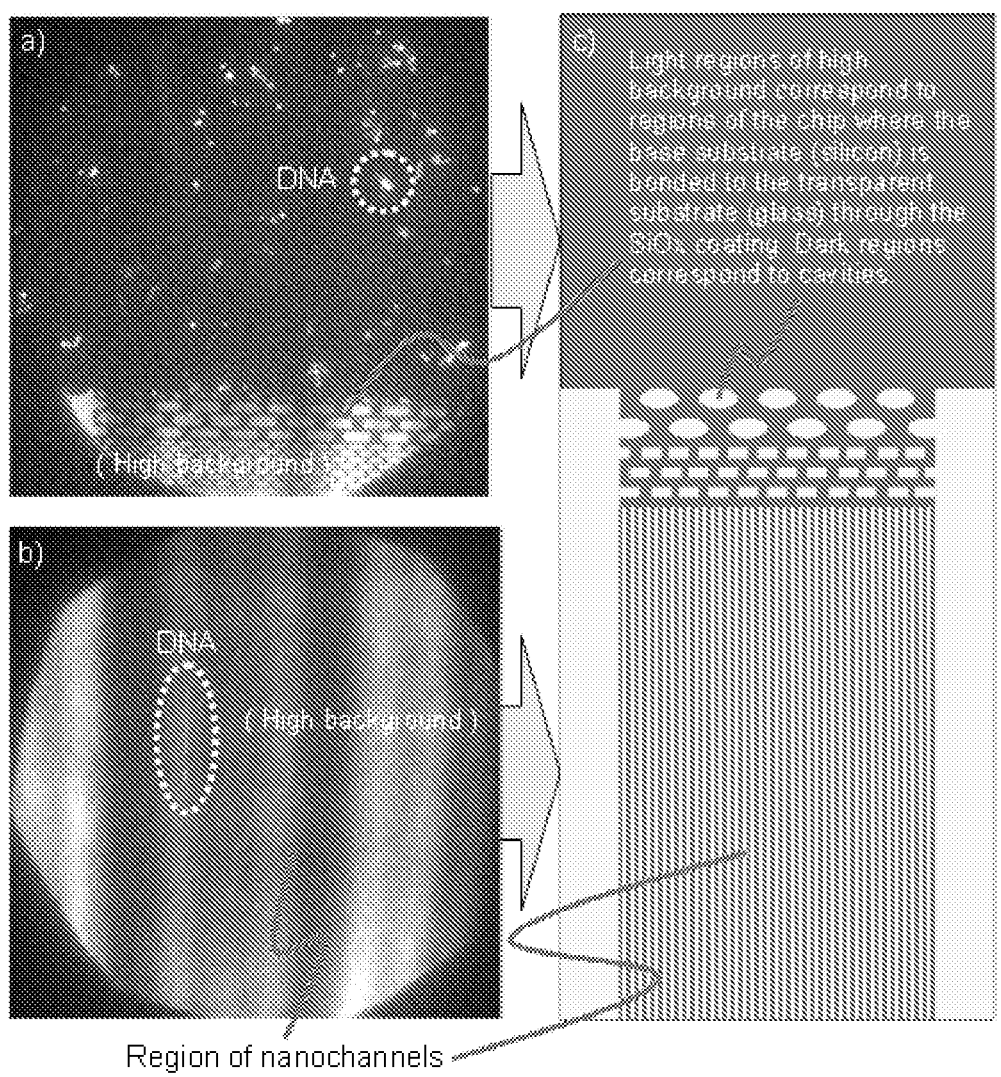
FIG. 20 illustrates images taken at excitation radiation wavelengths of about 653 nm of a nanochannel array having a $SiO_x$ thin film disposed at the bottom of the array and of TOTO-3 labeled DNA residing within that array.
Figure 21:
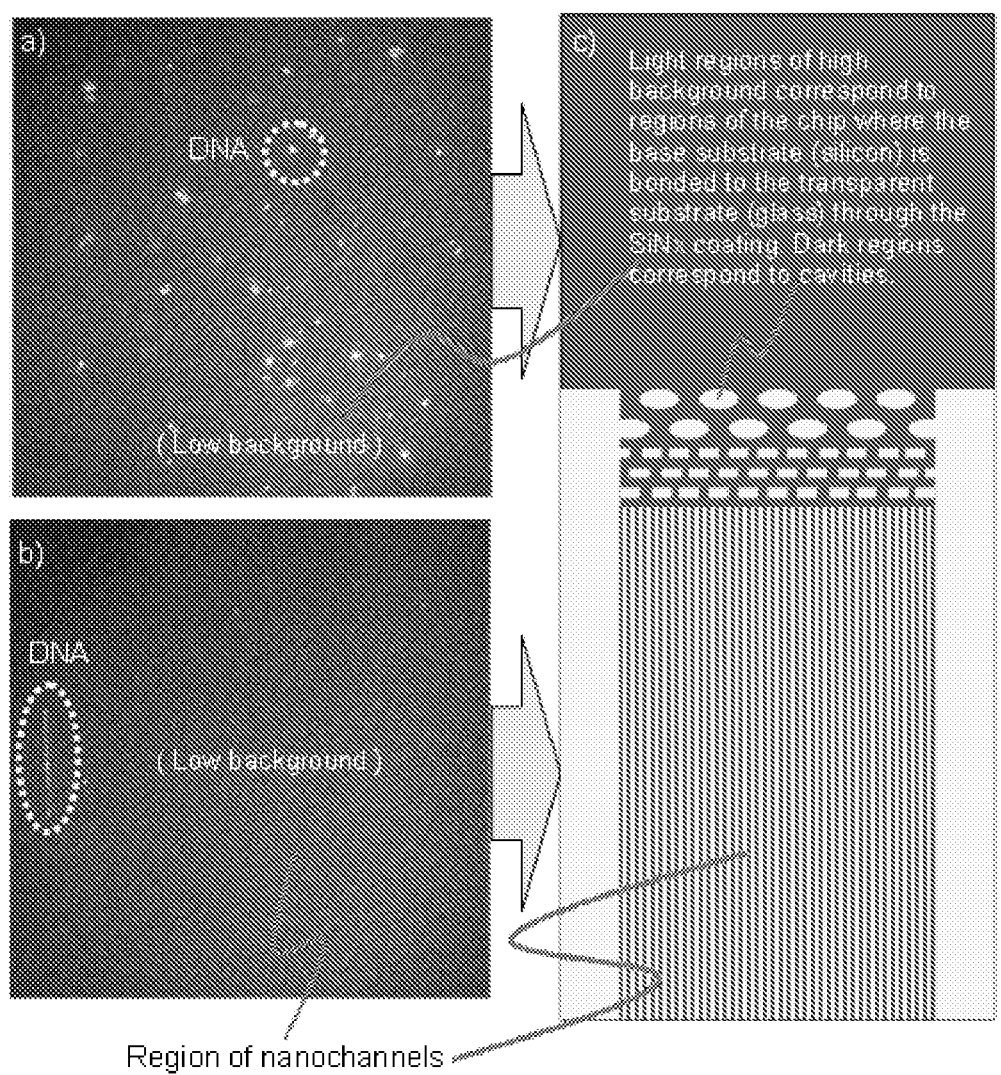
FIG. 21 illustrates images taken at excitation radiation wavelengths of about 653 nm of a nanochannel array having a $SiN_x$ thin film disposed at the bottom of the array and of TOTO-3 (fluorophore) labeled DNA residing within that array.

The confined channel's width can vary from about 5 nm to about 5 mm within the channel. The confined channel depth suitably varies from about 5 nm to about 1 mm within the channel. The confined channel width can vary from about 5 nm to about 50 microns within the channel, and the confined channel depth of from about 5 nm to about 50 microns within the channel. In some embodiments, the channel defines a channel of uniform depth and cross-section, although a channel may have a varying depth or cross-section as may be dictated by the needs of the user. As one example, a channel may narrow from a comparatively wide inlet down to a narrower passage or channel, or may broaden from a narrow inlet. The channel may, as shown in the attached figures, include various obstacles or other structures that extend from the channel's floor to its ceiling, or extend along at least part of the channel's height, as shown in FIG. 20 and FIG. 21, which figures show (looking downward) the tops of obstacles that are ochannel or rectangular in cross-section. Obstacles may be pillars, curves, and the like.

The confined channels suitably contain the bodies of interest in a medium, which medium can be a fluid, e.g., a liquid. Suitable media include gas, liquid, solids, plasma, vacuum, vapor, colloids, combinations thereof, and the like. The medium can be a buffer, a preservative, and the like.

Channels can be singular or multiple, and two or more channels may be connected to one another and, in some embodiments, may be connected to a common reservoir. The channels may be arrayed or multiplexed so as to allow for simultaneous analysis of multiple analytes. Methods for making such channels include nanoimprint lithography, photolithography, electron beam lithography, interference lithography, shadow masking, holographic lithography, ion beam lithography, and other methods known to those of skill in the art.

Channels are suitably channels of square or rectangular cross-section (as shown in, e.g., FIG. 13), but may be of circular, ovoid, or irregular cross-section, as dictated by the needs of the user or by process constraints. The cross-section of a channel may vary along one or more dimensions.

Nanoparticles, fluorophores, and the like may also be disposed within the channels. Moieties capable of interacting with a macromolecule disposed within (or translocated through) a nanochannel may be disposed within the channels so as to give rise to devices capable of generating a signal based on the interaction of a part of a macromolecule with an item disposed within a channel.

Channels may also include one or more inlets or outlets. Such features may allow for access to the channel from the side, from above, from below, or in essentially any orientation. Devices having channels and other fluidic elements disposed in two or three dimensions are within the scope of the claimed invention, and channels are suitably in fluid communication with one or more inlets, outlets, or both.

Base Substrate

The base substrate is composed of any substrate material that is semiconducting, insulating, or conducting, and is suitably capable of being bonded to the transparent substrate through the bottom thin film, the top thin film, or both.

The base substrate need not be transparent to the electromagnetic frequencies of interest. While silicon is especially suitable, other material choices include SiGe, Ge, strained silicon, GeSbTe, AlGaAs, AlGaInP, AlGaN, AlGaP, GaAsP, GaAs, GaN, GaP, InAlAs, InAlP, InSb, GaInAlAs, GaInAlN, GaInAsN, GaInAsP, GaInAs, GaInN, GaInP, GaSb, InN, InP, CdSe, CdTe, zinc selenide (ZnSe), HgCdTe, ZnO, ZnTe, zinc sulfide (ZnS), aluminum, aluminum oxide, stainless steel, Kapton™, metal, ceramic, plastic, polymer, sapphire, silicon carbide, silicon on insulator (SOI), astrositol, barium borate, barium fluoride, sillenite crystals BGO/BSO/

BTO, bismuth germanate, calcite, calcium fluoride, cesium iodide, Fe:LiNbO$_3$, fused quartz, quartz, fused silica, glass, SiO$_2$, gallium, gadolinium garnet, potassium dihydrogen phosphate (KDP), KRS-5, potassium titanyl phosphate, lead molibdate, lithium fluoride, lithium iodate, lithium niobate, lithium tantalate, magnesium fluoride, potassium bromide, titanium dioixde, sodium chloride, tellurium dioxide, zinc selenide, spin-on glass, UV curable materials, soda lime glass, any compound above in an hydrogenated form, stoichiometric variations of the above compounds, and the like, and any combinations thereof.

A substrate's thickness is suitably between about 0.01 mm to about 5 mm. The thickness can also be between about 0.1 mm and about 1 mm.

While a variety of labels may be used to analyze bodies of interest, light-emitting labels are well-known in the art and are considered especially suitable for use with the claimed invention Light emitting labels used to analyze the bodies of interest are typically excited by means of fluorescence, luminescence, chemi-luminescence, phosphorescence, and the like; fluorescence is a commonly-used method. Suitable labels include organic fluorophores, quantum dots, metal dots, polymer beads, lanthanide chelates, nanoparticles, fluorescent beads, phosphorescent beads, semiconductor nanoparticles, dendrimers, molecular antennae, and the like, and any combination thereof. TOTO-3 is an exemplary fluorophore; other fluorophores may be used.

Targets for analysis suitably include molecules, macromolecules, single stranded DNA, double stranded DNA, single stranded nucleic acid polymers, double stranded nucleic acid polymers, RNA, polymers, monomers, enzymes, proteins, peptides, conjugate macromolecules, self-assembled macromolecules, pieces of cellular components, organelles, viruses, and the like and any combination thereof. The present invention is considered especially suitable for use in DNA analysis.

The present invention also provides methods of reducing the background signal of an analysis device, the methods including disposing a bottom thin film on a base substrate, transparent substrate, or both, the base substrate further defining at least one boundary of a channel; the bottom thin film being capable of reducing the signal of the channel emitted at a particular wavelength of electromagnetic radiation.

The wavelength of the excitation light is in the range of from about 1000 nm to about 300 nm. Depending on the use of fluorescent labels, the excitation wavelength may be chosen for optimal excitation of the label. For example, TOTO-3 labels are suitably excited by light in the red (e.g., 635 nm) range, and the signal that may be detected from such excited labels may be sent through a band-pass filter (665-705 nm) to remove reflected excitation light.

Bonding

The bonding process can be any suitable process that bonds the transparent and the base substrates. In some embodiments, the bonding process is anodic bonding. Other bonding processes include, but are not limited to: fusion bonding, thermal bonding, direct contact bonding, plasma-activated bonding, direct oxide bonding, polymer bonding, metal-metal bonding, thermo-compression bonding, eutectic bonding, chemically-activated bonding, ultrasonic bonding, dielectric polymer bonding, adhesive bonding, van der Waals bonding, and any combination thereof.

EXAMPLES AND NON-LIMITING EMBODIMENTS

Example 1

Figure 18:
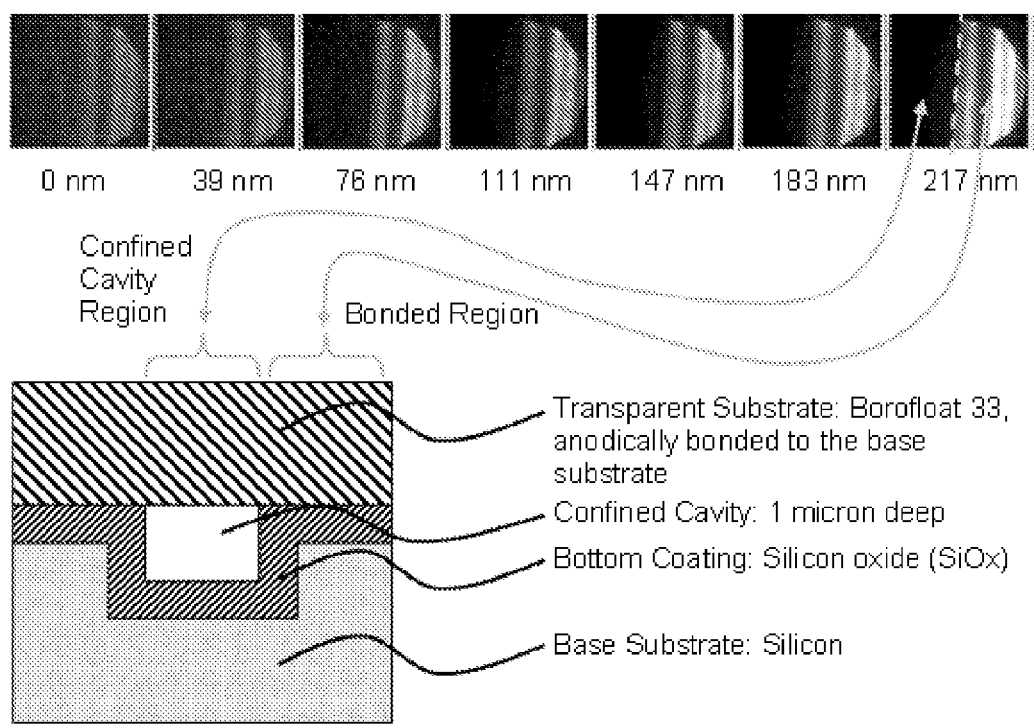
FIG. 18 illustrates background measurements taken at radiation wavelengths of from about 0 nm to about 217 nm of confined channels having a $SiO_x$ thin film disposed at the bottom of the channel.

FIG. 18 shows a series of fluorescent images taken of the edge of the confined channel, showing both the channel and the bonded regions. The excitation wavelength is red light (635 nm), and the detected signal is passed through a band-pass filter (665-705 nm) to remove any reflected excitation light. As the silicon oxide thickness was increased, the background in the region where the transparent substrate and base substrate are bonded through the thin film produced an elevated amount of background in the wavelength region above 635 nm, whereas the channel region maintains low background. It should be noted that the background level measured with green light (532 nm) and blue light (473 nm) showed no variation with silicon oxide thickness. In this example, the silicon oxide was deposited using PECVD and the channel was filled with air. Images were taken with an EMCCD camera.

FIG. 18 thus illustrates the challenges posed by using a thin film layer that produces a background signal when exposed to radiation that may also be used to elicit emission from a particular label. As shown in FIG. 18, the device with SiO$_x$ thin film produces a comparatively high background level across a range of wavelengths, which poses to users who might seek to analyze signals from labeled samples that emit (when exposed to excitation radiation) radiation in the same wavelength as the background signal from the device. Put another way, the SiO$_x$ device illustrated in this figure has a comparatively low signal/noise ratio, which would pose challenges for users seeking to pick out and analyze labeled samples against the comparatively high background signal from the device.

The higher background level makes detection of weak signals from bodies of interest close to the edge in the channel difficult or impossible. This is particularly problematic when the channel width is very narrow (approaching the wavelength of the excitation radiation or less, as is the case when the channels are nanochannels), in which case the labeled body of interest must have sufficient signal strength to overwhelm the background. However, as previously stated, removing the silicon oxide thin film to reduce the background will result in quenching of the labeled bodies.

Example 2

FIG. 19 shows the same experiment as FIG. 18, except that the silicon oxide thin film was replaced with a silicon nitride thin film. Silicon nitride was chosen as it is a dielectric material commonly used in the semiconductor industry, and thus widely available in most semiconductor foundries. In this example, there is no associated increase in background with nitride thickness.

FIG. 19 depicts a series of fluorescent images taken of the edge of the confined channel, showing both the channel and the bonded regions. The excitation wavelength is red light (635 nm), and the detected signal is passed through a band-pass filter (665-705 nm) to remove any reflected excitation light. As the silicon nitride thickness is increased, the background in the region where the transparent substrate and base substrate are bonded through the thin film shows no apparent increase or decrease. The background level measured with green light (532 nm) and blue light (473 nm) showed no variation with silicon nitride thickness. In this example, the silicon nitride was deposited using PECVD and the confined channel was filled with air. Images were taken with an EMCCD camera.

Example 3

In this example, illustrated by FIG. 8, double stranded human genetic DNA labeled with an intercalating dye (TOTO-3) was flowed in fluid through confined channels of various widths with a 58 nm $SiO_x$ thin film. As the widths of the channels decreases, the DNA becomes less visible due to the high background levels from the regions where the base substrate is bonded to the transparent substrate through the $SiO_x$ thin film.

FIG. 20 shows (a) a fluorescent image of DNA in confined channels of various widths. The boundary between the channels and the bonded regions are clearly visible due to the high background generated in the bonded regions, and (b) a fluorescent image of DNA in channels of width 100 nm. At this width, the DNA is barely visible due to the background originating from the bonded regions (i.e., regions where one substrate is bonded to another). The background appears to be uniformly high due to the very narrow widths of the nanochannels. Section (c) of the figure shows a schematic of the fluidic chip from which images (a) and (b) were acquired. The $SiO_x$ was deposited to a thickness of 58 nm over an etched silicon substrate using PECVD, and the transparent glass substrate composed of Schott Borofloat 33™ was anodically bonded to the $SiO_x$ covered silicon. The TOTO-3 labeled DNA excited with red light (635 nm), and the detected signal was passed through a band-pass filter (665-705 nm) to remove any reflected excitation light.

As shown in the figure (e.g., FIG. 20(b)), the $SiO_x$ thin film results in a device having comparatively high background signal (at the relevant wavelength) relative to the labeled sample. This relatively high background renders difficult the detection of weak signals from bodies of interest (e.g., labeled DNA) close to the edge in the channel. This phenomenon is particularly acute when the channel width is very narrow, such as when the width approaches the wavelength of the excitation radiation or even less, as is the case when the channels are channels of nanoscale width. In these instances, the labeled body of interest must have sufficient signal strength to overwhelm the background, but there may be limits on the number and brightness of the labels that can be placed on the body of interest, as well as limits on the intensity of the radiation that can be used to excite the labeled body. Further, as explained elsewhere herein, removing the silicon oxide thin film to reduce the background may then result in quenching of the labeled bodies, making analysis more difficult.

Example 4

In this example, shown in FIG. 21, DNA labeled with an intercalating dye (TOTO-3) is flowed in fluid through confined channels of various widths with a 58 nm $SiN_x$ thin film. As the widths of the channels decreases, the DNA remains visible, as the background levels do not increase in the regions where the base substrate is bonded to the transparent substrate through the $SiN_x$ thin film, as compared with the $SiO_x$ thin film in FIG. 20.

FIG. 21 shows at section (a) a fluorescent image of DNA in confined channels of various widths. Unlike FIG. 20(a), the channel boundaries are not visible due to the low background. FIG. 21(b) illustrates a fluorescent image of DNA in channels of width 100 nm. The SBR of the labeled DNA is significantly higher than that shown in FIG. 20(b). FIG. 21(c) is a schematic of the enclosed channel chip from which chip images (a) and (b) were acquired.

In this non-limiting embodiment, the $SiN_x$ was deposited to a thickness of 58 nm over an etched silicon substrate using PECVD. Transparent glass substrate composed of Schott Borofloat 33™ was anodically bonded to the $SiO_x$ covered silicon substrate. TOTO-3 labeled DNA was excited with red light (635 nm), and the detected signal was passed through a band-pass filter (665-705 nm) to remove any reflected excitation light.

Comparing the $SiN_x$ thin film (FIG. 21) to the SiOx thin film (FIG. 20) also serves to highlight another aspect of the claimed invention. As shown in FIG. 20 and FIG. 21, a $SiN_x$ thin film (as compared to a $SiO_x$ thin film) allows the fluorescently labeled molecules under study to fluoresce when illuminated by excitation radiation, rather than the molecules being quenched and at least partially losing their ability to emit radiation of an emission wavelength.

Thus, in some embodiments, one or more of the thin films is selected for its ability to reduce the background signal of the analysis device (compare FIG. 18—illustrating the background signature for a sample device using $SiO_x$ as a thin film—with FIG. 19—showing the background signature for a sample device using $SiN_x$ as a thin film). The thin film may further be chosen for its ability to allow a fluorescently labeled target to fluoresce when excited without quenching that label's fluorescence (compare FIG. 20(b)—illustrating the quenching effect that the substrate may exert on a fluorescently labeled sample with FIG. 21(b)—illustrating the lack of quenching present with a $SiN_x$ thin film).

Without being bound to any particular theory, a particular thin film material may shield the fluorescent molecules from radiation that may be reflected from the substrate (or other source) during the fluorescent molecules' exposure to excitation radiation. Also without being bound to any particular theory of explanation, the thin film material may accomplish its reduction of the background signal from the device by shielding or absorbing radiation of a particular wavelength that may be reflected from the substrate during the fluorescent molecules' exposure to excitation radiation.

While the disclosed, non-limiting embodiments highlight the advantages of the claimed invention during analysis of TOTO-3—labeled DNA excited with red light (635 nm) disposed within a device having a $SiN_x$ thin film and Si and Borofloat 33™ substrates, the invention is not limited to this sample embodiment. As described elsewhere herein, the substrates and thin films of the claimed invention may include many different materials, and the optimal combination of thin film, label/fluorescence and substrate for a particular method of analysis will be easily found by the user of ordinary skill. In some embodiments, the invention allows for a user—by selection of an appropriate thin film—to reduce the background signal of a device, to reduce the quenching that a device may effect on fluorophores disposed within the device.

As explained elsewhere herein, quenching or otherwise limiting the ability of a fluorophore or other label to reflect or emit radiation may be undesirable because such quenching limits the ability of the user to resolve the target against the background. By avoiding (or at least reducing) such quenching, the present invention enhances the ability of the user to resolve the presence or position of such labels against the background. $SiN_x$ is one material that does not quench fluorophores' ability to fluoresce (while also reducing the background of the analysis device, as shown in FIG. 7 and FIG. 21). Other materials that reduce the background while also minimizing quenching will be easily identified by the user of ordinary skill in the art.

In some embodiments, the device includes a channel or chamber disposed in a chamber material (e.g., $SiN_x$) that is itself a comparatively low-background material that minimizes the quenching of fluorophores that are exposed to excitation radiation while disposed within the chamber. Such chambers may be formed in the material by, for example, disposing a sacrificial material within the chamber material and selectively removing the sacrificial material so as to leave behind a channel that substantially conforms to the removed sacrificial material.

Exemplary Embodiments

FIG. 1 depicts a schematic view of a device according to the claimed invention. The device in that figure includes two substrates, A and B, bonded to one another. Substrate A has a thickness of $D_A$, and substrate B (the upper of the two substrates) has a thickness of $D_B$.

As shown in the figure, a port (which may be an inlet or outlet) extends through substrate A or B so as to place the nanoscale structures on the device in fluid communication with the environment exterior to the device. In some embodiments, the port extends through the entirety of the device, and in some embodiments allows introduction (or removal) of fluid from Interconnects—which may be microscale channels or conduits—place the port in fluid communication with the front-end (FE) structures located on the device. A port may extend through the full thickness of a substrate or partially through the substrate's thickness.

The FE structures may act to partially extend or elongate a macromolecule (such as DNA) that may be analyzed in the device. Macromolecular elongation is further explained in U.S. application Ser. No. 10/484,293, the entirety of which is incorporated herein by reference. Suitable FE structures are described elsewhere herein, and can include crow-form channels, eagle-form channels, pillars, posts, and other structures that may act to elongate a tangled or folded body that is flowed against or through the structures. Such structures are suitably patterned on one or both of the substrates.

Also shown in FIG. 1 is a nanochannel array device, which device may be fabricated on substrate A, substrate B, or some combination thereof (e.g., some parts of the array are fabricated on substrate A, and other parts being fabricated on substrate B). Suitable nanochannels and methods for analyzing macromolecules disposed in nanochannels are all described in U.S. application Ser. No. 10/484,293, the entirety of which is incorporated herein by reference.

In some embodiments, the analysis methods include exposing a DNA target to one or more labels, translocating the DNA target through a device according to the present application, and interrogating (e.g., optically) the DNA target for the presence (or absence) of the label. Fluorescent dyes and related instruments are considered suitable for such an analysis.

The nanochannel array may include one or more nanochannels, which may be arranged in parallel, serpentine, converging, diverging, zig-zag, curved, or other such patterns, as shown in the attached figures.

In one non-limiting embodiment, the nanochannel array includes a single nanochannel that doubles back on itself, as shown in FIG. 10. A nanochannel may be of constant or of varying cross-section, and multiple nanochannels present on the same device may be of different sizes.

The devices shown in FIG. 1 also, in some embodiments, include a back-end (BE) structure that may be disposed between the nanochannel array and a port, outlet, or other conduit. The BE structure is suitably of a configuration suitable for a FE structure (described elsewhere herein), and may include one or more channels, pillars, obstacles, and the like. Such BE structures suitably assist in transporting a target (e.g., a macromolecule) from a nanochannel analysis region to an interconnect or other conduit. The BE may assist in transporting a target from a nanoscale (e.g., nanochannel) environment to an environment that contains larger (micron-sized, or larger) structures.

Devices according to FIG. 1 may be of varying dimensions. The devices suitably have a length (L) of from about 0.1 mm to about 100 mm, a width (W) of from about 0.1 mm to about 100 mm, and the substrates (shown as A and B) suitably have a thickness in the range of from about 10 nm to about 10 mm. A given device may have from 1 to about 1000 independent nanochannel array devices, and a device may even have from about 2 to 500 individual ports. The optimal number of arrays and ports will depend on the needs of the user.

Figure 2:
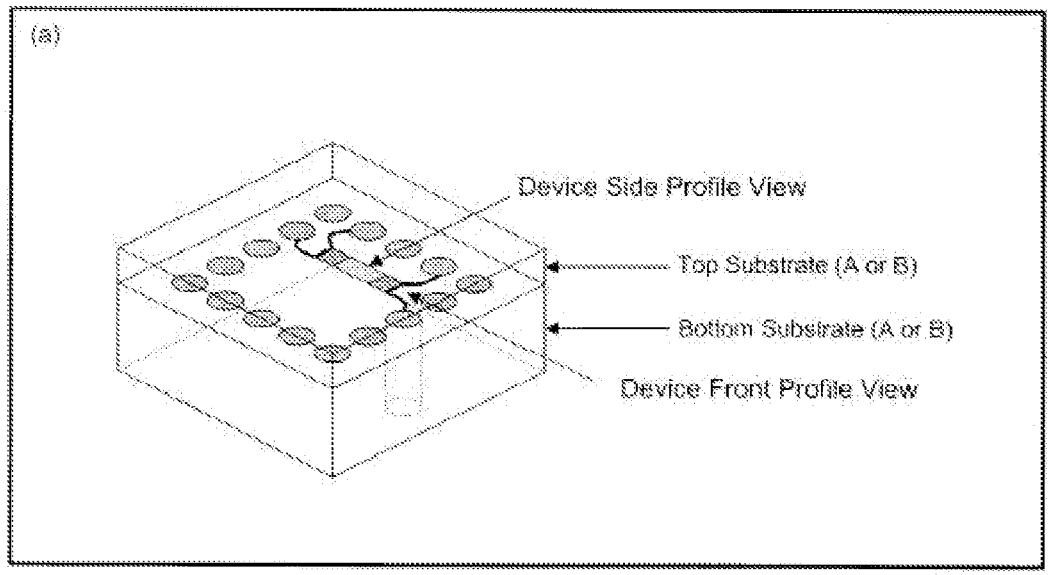
FIG. 2 depicts an exemplary device according to the claimed invention.
Figure 2:
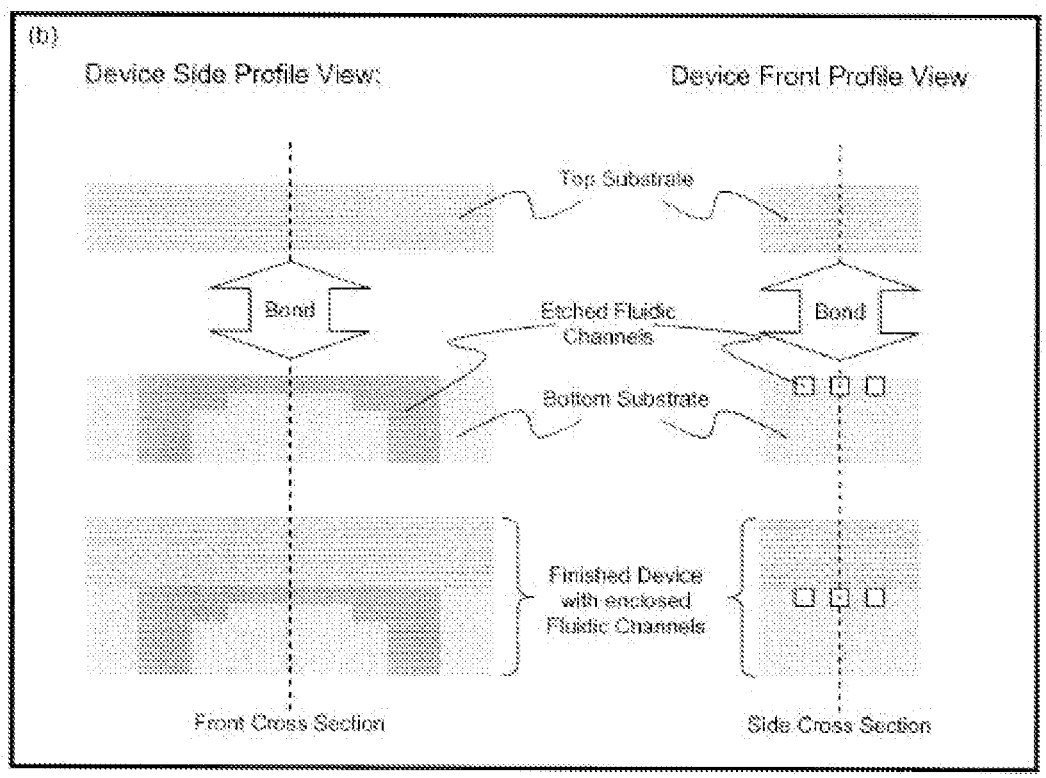
Figure 3:
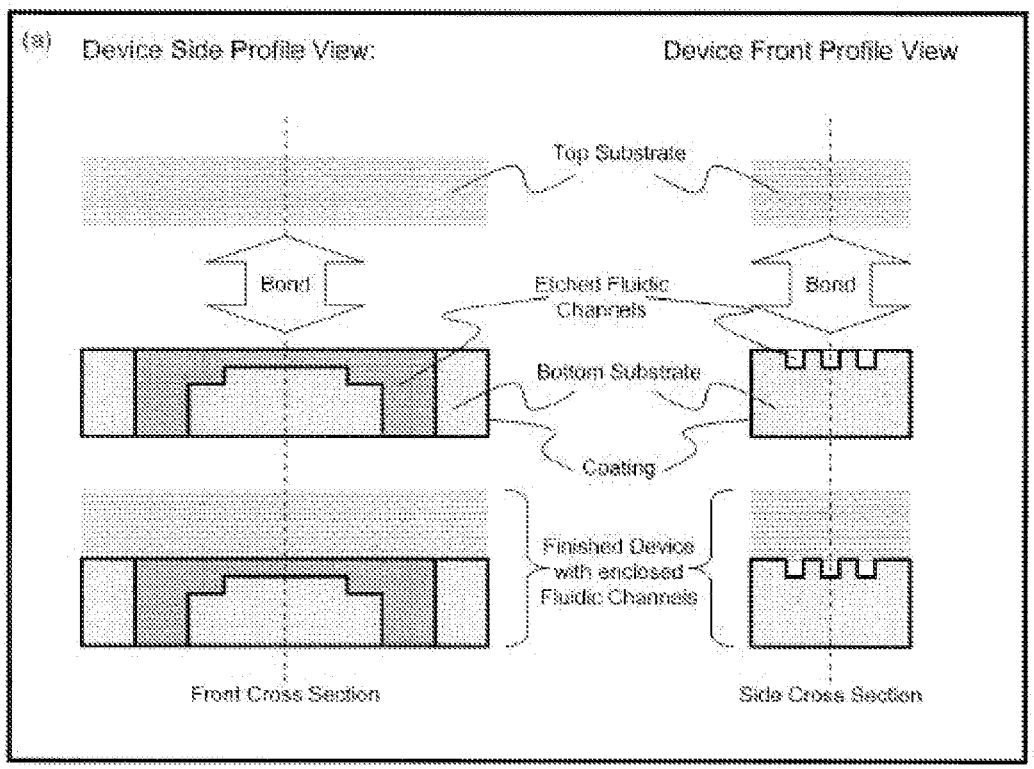
FIG. 3 depicts an exemplary fabrication scheme according to the claimed invention.
Figure 3:
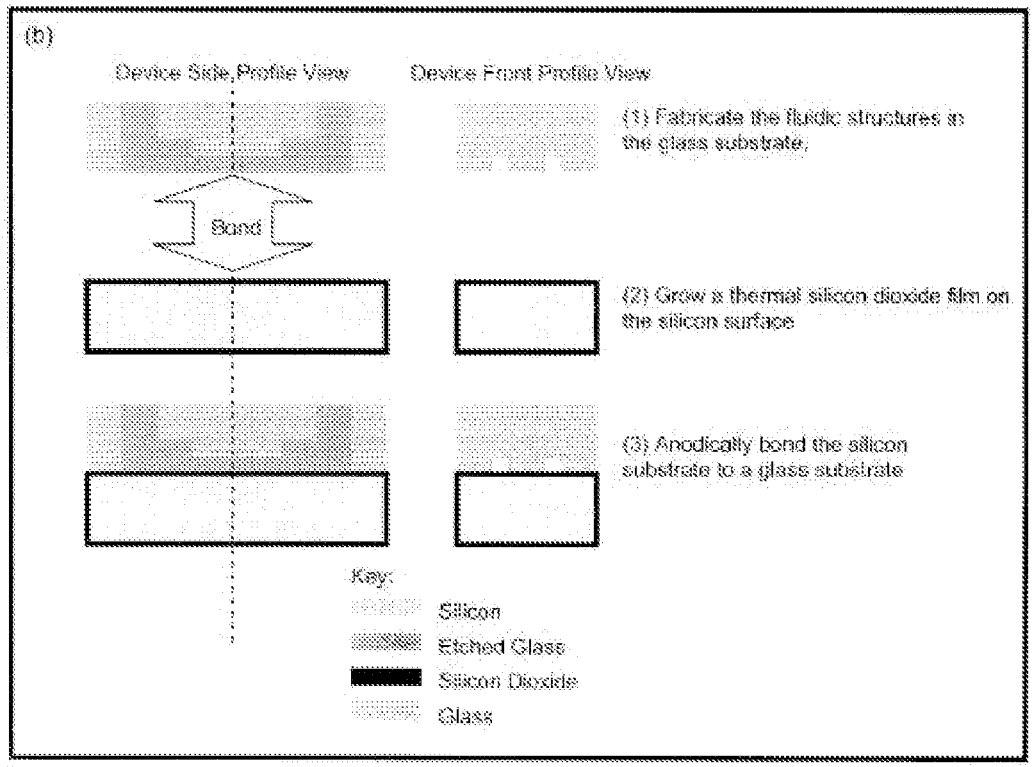

FIG. 2(a) depicts an exemplary nanodevice chip, with red arrows depicting the direction of the views of cross sections of the device illustrated in FIG. 2 through FIG. 5. FIG. 2(b) depicts an exemplary, non-limiting fabrication scheme according to the claimed invention. In this embodiment, fluidic elements are formed on the lowermost substrate and the lowermost substrate is then bonded (e.g., anodically bonded) to the upper substrate, which upper substrate can be glass or a suitable transparent material.

FIG. 3(a) shows an exemplary fabrication scheme, wherein one substrate (either substrate A or B) having channel elements etched thereon is coated either by growth of thermal oxide or conformal deposition methods such as atomic layer deposition (ALD) on the surface of the substrate, which is then bonded to a second substrate through fusion or anodic bonding. FIG. 3(b) shows a non-limiting fabrication scheme for a substrate with etched channel elements in the upper substrate, which upper substrate is suitably transparent glass and can be anodically bonded to a lower (e.g. silicon) substrate that has a film (e.g., silicon dioxide) thermally grown or otherwise deposited throughout the entire surface or only the bonded surface. Channels can be etched onto both substrates; when the substrates are bonded to one another, multiple channels result, or—if the channels on the substrates are in registration with one another—a single channel may be formed (FIG. 13).

FIG. 4(a) depicts an example fabrication scheme for two substrates (substrate A or B), with channel elements etched into both substrates, and then a subsequent step of coating the bottom substrate either by thermal oxide growth or conformal deposition methods such as ALD. The substrates are then bonded together through fusion or anodic bonding, with at least portion of the channel on opposing substrate surfaces overlapping. FIG. 4(b) depicts another non-limiting fabrication scheme, in which a layers of coating are deposited on both substrates, with channel elements then being etched into the coating layer and into the lower substrate, the substrates then being bonded together through fusion or anodic bonding, with at least portion of the channels on opposing bonded surfaces overlapping.

FIG. 5(a) depicts an exemplary nanodevice chip with arrows depicting the direction of the aerial view of the channel patterns on the device, illustrated at FIG. 5 to FIG. 11.

FIG. 5(b) depicts non-limiting layouts for a 4 port example embodiment and a 2 Port example embodiment configuration. The arrows indicate the direction of the sample (e.g., DNA) flow. The sample need not flow in the direction shown, and the flow direction may be stopped or even reversed as desired.

This embodiment depicts one suitable relationship between the ports, the interconnect regions, FE and BE regions, and a nanochannel array. By arranging these components in such a manner, the device enables manipulation of a target (e.g., DNA or another macromolecule) across a wide range of length scales, from the centimeter scale ($10^{-2}$ m) of the inlet port to the millimeter ($10^{-3}$ m) scale of the interconnects and FE/BE regions, on down to the nanometer ($10^{-9}$ m) range of the nanochannels in the nanochannel analysis region. While the analysis region is labeled "nanochannel array region" in FIG. 5, the analysis region may include a single nanochannel, or nanochannels that are not arranged in an array-like formation.

FIG. 6(a) depicts an example embodiment of a multi-port device design. The design in FIG. 6(a) has 16 ports, including 8 independent 2 port devices. FIG. 6(b) depicts a design having 16 ports, including 4 independent 4 port devices. These embodiments allow the user to simultaneously analyze multiple, different targets.

FIG. 7(a) depicts a multi-stage branched channel array. In this example, there are 5 stacked arrays of channels, the channels having progressively smaller cross sectional dimensions, and the channels being connected by 5 levels of forks bridging the microfluidic inlet channels and the nanochannel analysis region, located at the bottom of FIG. 7(a). The distance between the forks is suitably about 50 microns, and the two smaller channels suitably half the cross-sectional area of the original channel at each branch.

As shown, at each fork, the channel is divided into two smaller channels. The branch angle is suitably between about 30 and about 60 degrees, although it can range from about 0 to about 90 degrees, and M is suitably from about 0.4 to about 0.6 W. As a matter of nomenclature, embodiments—such as the device shown in FIG. 7—that have a channel split by a pointed or triangular fork structure are known as "crow" devices or "crow" channels, which are described in more detail elsewhere herein.

A target (e.g., a fluid-borne macromolecule) may pass through from 1 to 15 or more divided channels during analysis, and the length (L) of each branch channel can vary from about 5 to about 80 micrometers. The user may alter the number of forks and the relative size of a secondary channel to a primary channel so as to enable controllable movement for a target moving from the comparatively large inlet port on to the nanoscale nanochannel analysis regions of the claimed devices. Multi-stage divided-channel structures (FIG. 7) may be used.

FIG. 7(b) illustrates a Scanning Electronic Microscopy (SEM) image of a branched forks interconnecting two arrays of channels of different sizes. FIG. 7(c) shows a cartoon view of a branching fork design having a comparatively sharp split at the fork, although the angle at the fork can be from about 0 to about 90 degrees.

FIG. 7(d) is an image taken from a video of fluorescently labeled molecules moving inside the channels, highlighting the channels and interconnecting forks. FIG. 7(e) is a fluorescent image of singular, comparatively long genomic DNA molecules moving from large channels into branched narrower channels, where the molecules are elongated. The sharp split at the fork is seen, outlined by singular DNA molecules.

In FIG. 7, multiple "crow" structures are used, such that a macromolecule or other target that enters the interconnect region shown at the top of the figure will pass through 5 (or more) forks/splits before the target enters the nanochannel array region shown at the bottom of the figure.

As discussed, the distance between the forks can be about 50 microns (though the separation distance can be greater or smaller than 50 microns), and the smaller channels that emerge from each fork are each about half the size of the original channel at each branch. Thus, the total cross-sectional area available to a fluid contained within the secondary (or "branch") channels is approximately equal to the cross-sectional area of the primary (or "trunk") channel. By maintaining along the length of a branched channel device an essentially constant cross-sectional area available for fluid flow, the disclosed devices minimize the changes and disruptions in flow fields that can result from channels of narrowing or broadening cross-sectional area.

FIG. 8(a) depicts a schematic of a second design for an alternative, multi-level branched, interconnected channel array. FIG. 8(b) shows a Scanning Electronic Microscopy (SEM) image of one of the branched forks interconnecting two arrays of channels of different sizes.

FIG. 8(c) shows the branching fork design having a more rounded or contoured bend around the fork. FIG. 8(d) shows an image taken from video of fluorescently labeled molecules moving inside the channels, highlighting the channels and interconnecting forks, and FIG. 8(e) shows a fluorescent image of singular long genomic DNA molecules moving from large channels and being elongated into branched narrower channels. Two different levels of contoured bends at the forks can be seen outlined by singular DNA molecules.

For the fluorescent images were, the the DNA sample consisted of male human genomic DNA stained with an intercalating dye (YOYO-1) at a ratio of 5 base pairs per dye molecule. The DNA was suspended in 0.5×TBE buffer at a concentration of 5 ng/uL. DNA was flowed into the nanochannels using either capillary flow or via electric field with an applied voltage in the range of 0-50V. Excitation of the sample was performed using a light emitting diode and the fluorescence emission was collected through a 60× objective and detected using an electron multiplying CCD camera.

FIG. 8 thus depicts channels according to the "eagle" configuration. As shown, the fork that splits the primary channel into branch channels is suitably a rounded structure, such as rounded pillar. The diameter or effective cross-section of the fork is suitably such that the edge of the fork extends into the channel that precedes the fork.

Without being bound to any particular theory, in this configuration a macromolecule (or other target) that, in a channel, follows an electric field's path (e.g., from an applied gradient) will be more likely to enter the center of a following channel rather than the edge, as shown in the figure. Thus, targets will be less likely to enter certain channels over others in the branched network, and the result is a more uniform loading of the nanochannels in the nanochannel array.

In one example embodiment, M is 0.3 to 0.7 times W, and X is 0.2 to 0.5 times W. The number of forks the a target may traverse before reaching the nanochannel array can be from 2 to 15, and the length of each branch channel (L) can vary from 5 to 80 microns.

In some embodiments, multiple "eagle" structures are used, and the number of forks in each eagle structure is 5 before the target will enter the nanochannel array region. The distance between the forks in this non-limiting embodiment is 50 microns (though this distance can be greater or smaller than 50 microns), and the two smaller (branch) channels are half the original channel, such that the total cross-sectional area available for fluid flow is the same at any plane along the length of the device.

FIG. 9(a) shows a schematic of another design, showing a combination of branched channels and post arrays. In one embodiment, a branched channel arrays interconnect with one another, and within the channels are arrays of posts.

Figure 9:
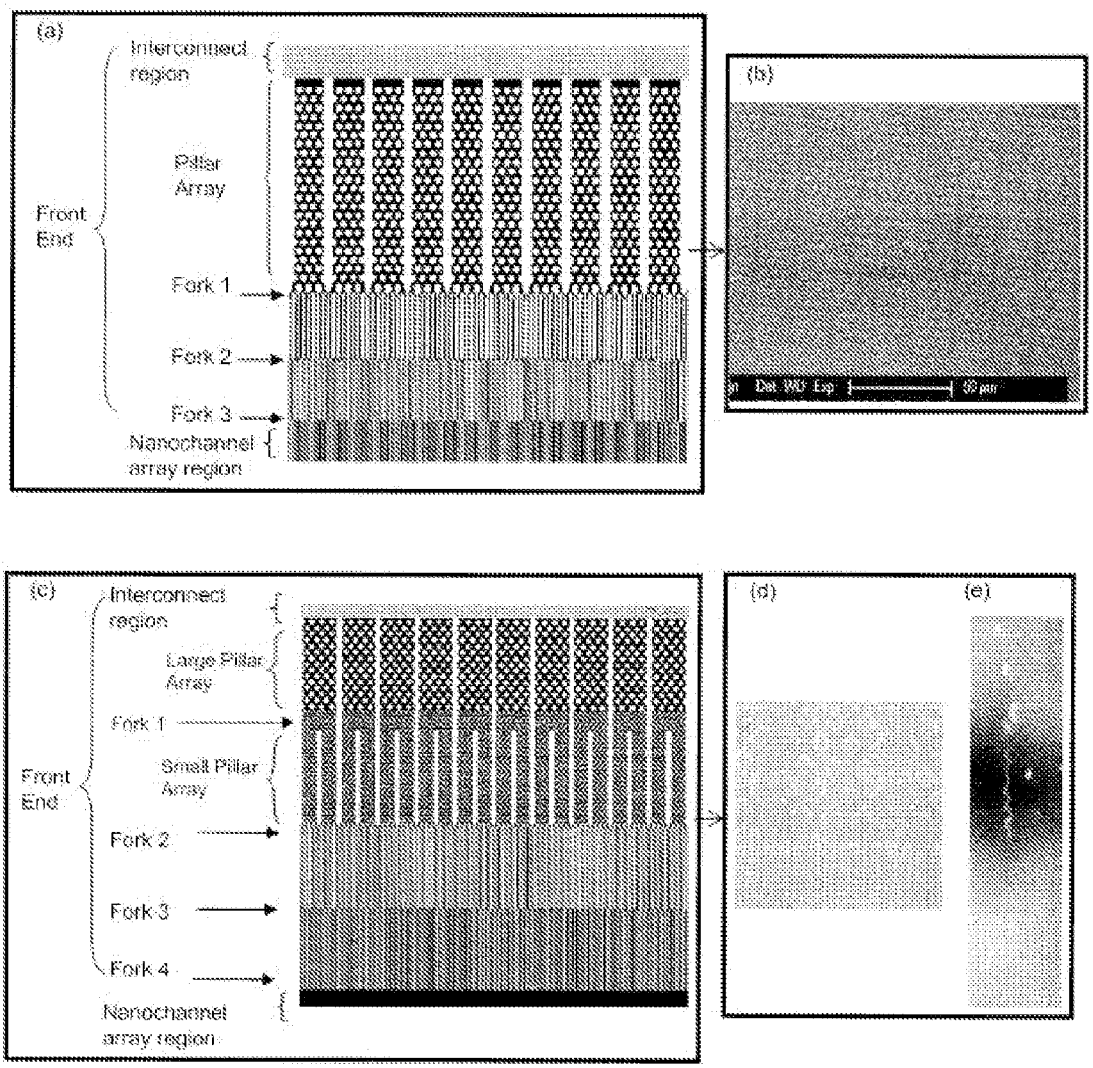
FIG. 9 illustrates a device design having a combination of branched channels and post arrays.

FIG. 9(*b*) shows a Scanning Electronic Microscopy (SEM) image showing dense round shaped post arrays embedded within channels.

FIG. 9(*c*) shows a schematic of a design having branched channels and post arrays. In one embodiment, with multi-level branched channels connecting to one another, there are arrays of diamond shapes posts of gradually reduced sizes and increased density. FIG. 9(*d*) shows a Scanning Electronic Microscopy (SEM) image showing dense post arrays embedded within channels interconnecting with downstream channels of smaller sizes. FIG. 9(*e*) shows a fluorescence image of comparatively long genomic DNA molecules moving within a post array with channels.

FIG. 10(*a*) depicts a design having a single long nanochannel arranged in a continuously connected, serial set of parallel nanochannels in a serpentine configuration; only a single set from an array of this configuration is shown here. FIG. 10(*b*) shows a Scanning Electronic Microscopy (SEM) image showing a boxed area of such a serpentine configured nanochannel etched into a silicon substrate, showing the turns of the channel. FIG. 10(*c*) shows a fluorescence image of a genomic DNA molecules moving within the nanochannel and making a 180 degree turn.

This configuration addresses, inter alia, the challenge of visualizing an elongated or elongating macromolecule in a single field of view. Because macromolecules may be very long, a channel of sufficient length to enlongate a macromolecule may be longer than the width of a high-magnification microscope's field of view. This in turn prevents the user from visualizing the entire macromolecule in a single field of view.

A device that has a nanochannel in a serpentine or switch-back pattern as shown in FIG. 10, however, increase the length of channel that fits within a single field of view and thus enables the user to view an elongated macromolecule in a single field of view. Alternatively, such a device enables a single field of view to cover a substantial portion of the elongated macromolecule. Serpentine, switch-back channels also increase the residence time of a translocating macromolecule within a single field of view.

FIG. 11(*a*) depicts multiple, long nanochannels arranged in a continuously connected serial set of parallel nanochannels, the difference from the previous figure being that each channel stage has a progressive reduction in its channel width, from 1000 nm down to 100 nm. FIG. 11(*b*) shows a Scanning Electronic Microscopy (SEM) image, with a boxed area of one set of such serpentine configured nanochannel etched into a silicon substrate, showing the gradually reduced width of the channels from bottom to top and then the comparatively wide channel outlet.

FIG. 11(*c*) shows a set of time-lapse video frames (each panel represents a different point in time) that track the fluorescent image of a single genomic DNA molecule moving within channels described in FIG. 11, the molecule having a progressively stretched length as it enters nanochannel regions of smaller and smaller sizes. To act as a control or reference standard, an image of a stationary molecule is shown, and the length of the stationary molecule is shown as outlined between the two dashed lines drawn across all of the panels of assembled frames. Turning to the various image panels, the uppermost panel shows a bright field optic image of the actual chip pattern, and the fifth panel shows a fluorescent image of the DNA molecule turning a corner.

FIG. 12(*a*) shows a Scanning Electronic Microscopy (SEM) image showing another non-limiting design, this design including an array of parallel, non-straight nanochannels arranged in a zig-zag pattern. FIG. 12(*b*) shows an image of fluorescently labeled DNA molecule stretched inside the zig-zag shaped channel. FIG. 12(*c*) shows a Scanning Electronic Microscopy (SEM) image of an arbitrary nanochannel pattern (the letters "BNM"), with the channels in the pattern all having an essentially equal channel width. FIG. 12(*d*) shows a Scanning Electronic Microscopy (SEM) image showing two sets of perpendicular nanochannels intersecting with each other, the overlapping region appearing as a dense, rounded post array.

Fabrication

The fabrication process may include fabricating fluidic features on a substrate surface, and then bonding the substrate surface to a secondary substrate to form an enclosed fluidic device accessible by the ports. Alternatively, the fabrication may include fabricating fluidic features on a substrate surface, and fabricating fluidic features on asecondary substrate surface, and then bonding the two substrate surfaces together to form an enclosed fluidic device accessible by the ports.

Substrate material can include, but is not limited to: silicon, silicon dioxide, silicon nitride, hafnium oxide, quartz, glass, fused silica, metal, aluminum oxide, metal, ceramic, polymer, plastic, dielectrics, SiGe, GaAs, GaAlAs, ITO, and the like. In one example embodiment, at least one of the substrates must be transparent to UV, visible, and infrared electromagnetic radiation.

In one example embodiment, the substrates are wafers of glass, silicon, and or quartz, and after bonding, the chips are obtained by dicing the bonded wafers. In one example embodiment, the fluidic elements are fabricated using methods known to the semiconductor, MEMS and microfluidic industry, including, but not limited to: photolithography, plasma etching, material deposition, wet etching, bonding, and any combination thereof.

In one example embodiment, the nanochannel array, front-end/back-end, and interconnects are patterned (e.g., via photolithography) onto a substrate (such as silicon), after which the patterns are transferred into the silicon by etching. A variety of patterning and etching options are possible:

Patterning may be accomplished by, e.g., photolithography, nanoimprint lithography, embossing, interference lithography, near field holography, contact printing, extreme UV lithography, electron beam lithography or any combination thereof.

For these patterning options, the use of a hard or soft mask can aid in the pattern transfer to the substrate. These masks include, but are not limited to: anti-reflection coatings, silicon oxide, silicon nitride, dielectrics, metals, organic films, combinations thereof, and the like. For all of these patterning options, various intermediate pattern transfer methods could be used, including, but not limited to: lift-off processes, shadow evaporation, growth, deposition, combinations thereof, and the like.

Etching options include—but are not limited to—chemical etching, wet etching, etching with KOH, etching with TMAH, etching with HF, etching with BOE, ion etching, reactive ion etching (RIE), plasma etching, plasma assisted etching, inductively coupled plasma (ICP) etching, bosch etching, patterned oxide growth in silicon (such as LOCOS) and removal with a wet etch, combinations thereof, and the like.

Patterning Order

In one example embodiment, the nanochannel array and Front-end/Back-end (FE/BE) are patterned and etched simultaneously, the interconnects being patterned later.

However, this need not be the case, and the order of patterning these fluidic elements can vary.

The nanochannel array can be patterned by interference lithography, and the front-end/back-end patterned by photolithography in a separate step. In another embodiment, the nanochannel array, front-end/back-end, and interconnects is suitably patterned in a single step using photolithography or nanoimprint lithography. In another embodiment, patterning technologies capable of transferring variable-depth features into the substrate such as nanoimprint or embossing are used to allow the interconnect, front-end/back-end, and nanochannel array to have different depths, all with a single patterning step.

Ports

Ports are suitably patterned by photolithography, and then etched with an etch process such as a deep silicon etch ("Bosch Etch"). However, a variety of fabrication options are available for fabricating ports. A non-limiting list of such options includes RIE, ICP etching, plasma etching, laser drilling, laser ablation, sand blasting, drilling, wet etching, chemical etching, water drilling, ultrasonic drilling, and any combination thereof.

The port suitably has a width (diameter) of 5 to 5000 microns, and the depth is the thickness of the substrate that it goes through. In one example embodiment, the port has a width (diameter) that ranges from 50 to 2000 microns.

Bonding

In one example embodiment, the fluidic elements of the device are completed by anodically bonding a patterned silicon substrate with an un-patterned glass wafer.

In one example embodiment, the glass wafer to be anodically bonded can be Pyrex 7740, Schott Borofloat 33™, Hoya SD2™, or any glass with similar thermal expansion characteristics. Other options are suitable, including (but not limited to) fusion bonding, thermal bonding, chemical bonding, quartz-quartz bonding, glass-glass bonding, polymer bonding, solvent bonding, adhesive bonding, combinations thereof, and the like.

Bonding conditions—anodic and otherwise—will be easily optimized by the user of ordinary skill in the art. As one non-limiting example, silicon and Borofloat™ glass may be anodically bonded together using a voltage of 400V, a temperature of about 350° C., applied for 5 min. Anodic bonding voltages may range, for example from about 200 V to about 800 V, temperatures suitably range from about 200° C. to about 400° C., and application time from about 1 to about 100 min.

Fluidic Element Surfaces

A variety of materials can compose the surface of the fluidic elements, including, but not limited to: silicon, silicon dioxide, silicon nitride, hafnium oxide, quartz, glass, fused silica, metal, aluminum oxide, metal, ceramic, polymer, plastic, dielectrics, SiGe, GaAs, GaAlAs, ITO, organic molecules, self-assembled monolayers, self-assembled multi-layers, combinations thereof, and the like. In one example embodiment, the fluidic elements will have a dielectric surface; in some embodiments, fluidic elements will have a silicon dioxide and/or glass surface.

Fabrication Example

In one non-limiting embodiment, fluidic elements (nanochannel array, front-end/back-end, interconnects, and ports) after bonding have a silicon dioxide or/and glass surface, such that fluid disposed within the resultant device contacts only silicon dioxide or/and glass. This surface is formed by depositing a film of silicon dioxide over the etched silicon surface after the patterning and etching of the nanochannels, front end/back-end, interconnects, and ports.

An oxide is deposited by atomic layer deposition (ALD) on the patterned and etched silicon substrate, and has a thickness from about 1 nm to about 5000 nm. This silicon wafer is then anodically bonded to a glass substrate.

The silicon dioxide surface serves several useful purposes. First, the silicon dioxide provides an insulated film which is useful when an electric field is used to drive the movement of DNA in the fluidics, and one of the substrates is silicon.

The silicon dioxide also provides a surface that can be functionalized and or passivated as required by the application. The layer further allows the nanochannel cross-section to be modified (tailored) to the desired size when the oxide is grown or deposited on the preexisting etched nanochannel.

In one example, a 200 nm wide and 150 nm deep nanochannel is reduced to 100 nm wide, and 100 nm deep when 50 nm of conformal oxide is deposited over the nanochannels. In this way, application of a coating to an already-formed fluidic element (e.g., a groove or trench) allows the user to controllably build up the boundaries of that element so as to reduce the cross-section of that element that is available to fluid flowing therein.

Silicon dioxide is also transparent to a wide spectrum of electromagnetic radiation, including UV, visible and infrared light.

There is a wide variety of fabrication options for forming fluidic channels with a silicon dioxide and/or glass surface. These include (but are not limited to):

Thermal Oxide Growth on Silicon

If one of the substrates to be used is silicon, the silicon dioxide surface can be achieved by growing the oxide using the silicon surface as a source of silicon. Examples include, but are not limited to: dry thermal oxide growth, wet thermal oxide growth. This applies irrespective if all, some, or none of the fluidic elements are to be patterned and etched in the silicon. Non-limiting, silicon-based embodiments are set forth in the attached figures.

Deposited Oxide on Silicon, Glass, or Quartz

The oxide can be deposited on one or both of the substrates. Examples include, but are not limited to: PECVD, CVD, LPCVD, thermal evaporation, spin-on glass, e-beam evaporation, sputtering, ALD and any combination thereof. Representative examples are shown in, e.g., FIGS. 2-5.

Etching Directly into Silicon Dioxide, Quartz, or Glass

Furthermore, a silicon dioxide or glass surface can be achieved by etching the fluidic elements directly into silicon dioxide or glass. This can be done by etching directly into the silicon dioxide/quartz/glass substrate, or etching into a film of silicon dioxide on a silicon substrate. See, e.g., FIGS. 2-5.

Device Configuration

In FIG. 5, the primary input and output ports opposite one another such that if an electric field were to be applied, the field strength would be approximately equal in all of the nanochannels of the nanochannel array. In one example embodiment, all three fluidic elements of the device: nanochannel array, frontend/back-end, and interconnects are included.

In another example embodiment, the front-end and/or back-end could be omitted, with the interconnects connected directly to the nanochannel array. In another example embodiment, the interconnects could be omitted, with the front-end and/or back-end connecting directly to the ports.

In another example embodiment, both the front-end and back-end and the interconnects could be omitted, thus having the nanochannel array connecting directly to the ports. In an example embodiment, the device is symmetrical so as to maximize the uniformity of the electric field strength though the nanochannels in the nanochannel array when an electric field is applied between the inlet and outlet ports.

In another example embodiment, the outlet of the nanochannel array leads to an inverted frontend structure (called the back-end or BE), and then into the interconnect channels as in FIG. 5(b). In another example embodiment, the outlet of the nanochannel array leads directly to the outlet port (omitting the back-end and interconnects).

In another example embodiment, the outlet of the nanochannel array could lead directly to an interconnect that leads to the outlet port (omitting the back-end). In another example embodiment, the back-end could lead directly to the outlet port (omitting the interconnects).

2-Port Device

The 2 Port chip has one input in which the sample is loaded, and one output in which it is subsequently removed. Sample movement is directly controlled via these two ports using forces such as electroosmotic, electrokinetic, electrophoretic, pressure, capillary, or any combination thereof. This design has significant advantages including simple ease of handling for direct capillary sample loading. The design also minimizes the number of ports, and thus maximizes the number of independent devices allowable per chip.

4-Port Device

The 4-port device has two input (primary/secondary) ports, and two output (primary/secondary) ports. The principal advantage of this design over the 2-port chip is to provide the chip operator more degrees of freedom in controlling the sample movement through the nanochannel array. Sample movement can be directly controlled via these four ports using forces such as electroosmotic, electrokinetic, electrophoretic, pressure, capillary, combinations thereof, and the like. In this application, the sample is flowed from the primary to the secondary inlet port in a controlled manner, and once an item of interest is identified, it can be translocated into the nanofluidic FE region by modulating sample flow.

Gradient Front End and Back End

The Front-End and Back-End are characterized as the interfaces between the microfluidic and the nanofluidic regions. The front end (FE) suitably facilitates the unraveling, elongation, and transition of the DNA from the microfluidic-scale interconnect region into the smaller-scale nanochannel array. This is suitably accomplished by flowing the DNA through a network/array of densely patterned, progressively smaller (and more closely spaced) structures, which effects DNA elongation as the DNA approaches and then enters a nanochannel or nanochannel. FE designs are suitably a variant of the "branched channel network" structure, which structure has several attributes.

First, with each branch, the channel is split into two or more channels. In one embodiment, the total widths of the branching channels are approximately equal to the original, such that the total cross sectional area remains approximately the same. In this manner, flow rate throughout the branched channel network should remain approximately constant.

Second, by progressively splitting, the branched network promotes uniform loading of DNA into the nanochannell array, i.e., there is no biasing of a particular nanochannel, or set of nanochannels within the nanochannel array.

Further, the branched channel network presents progressively smaller fluidic channels that efficiently untangle and elongate very long segments of DNA.

At a given branch point, the branching channels need not be the same width, length, or depth. Nor do they have to be parallel to each other, or uniformly distributed. Nor do the branched channels have to be straight or linear in configuration. In some embodiments (FIG. 9, for example), to further enhance their ability to untangle the DNA, the branch channels may contain pillar structures.

The FE fluidic structures are approximately 10-1000 nm deep, and up to 10000 nm wide. A channel (or a pillar or other obstacle) in a FE structure can also have a depth of from about 100 to about 500 nm, or even about 200 nm to about 300 nm. Structures (e.g., channels, pillars, and the like) can also have a width in the range of from about 1 to about 10,000 nm, or from about 20 nm to about 5000 nm, or from about 50 nm to about 1000 nm, or even from about 100 nm to about 500 nm.

Because the purpose of these structures is to gradually confine the DNA sample from the microfluidic environment to the nanofluidic environment, in one example embodiment these fluidic structures have a depth that spans from 1000 nm to the depth of the final nanochannel, and a width that spans from 10000 nm to the width of the final nanochannel. However, this reduction in feature size in the FE structure need not be monotomically decreasing, nor may it require a continuous variation in feature sizes. For example, a change in the feature sizes (depth and width) of the FE can be done in steps.

"Crow" Configuration

In the "crow" embodiments shown in FIG. 7, the branched channel FE design includes a comparatively sharp fork (splitter) that splits the channel into two new channels. The new channels can be the same size, or smaller than the original channel. The branching angle can vary from 0 to 90 degrees. The length of the branched channels can vary from 5 to 500 microns. Each branching stage need not be the same length.

"Eagle" Configuration

The "eagle" design differs from the "crow" design. First, the fork is shaped as a rounded pillar. Second, the diameter of the pillar fork is such that edge of the pillar protrudes into the channel that precedes it. The purpose behind this design is that a macromolecule (or other target) following an electric field path (or other gradient) will be more likely to enter the center of the succeeding channel (rather than along the edge). In this way, targets are less likely to bias certain channels over others in the branched network, and will instead result in a more uniform loading of the nanochannels in the nanochannel array. The "eagle" configuration (like the "crow" configuration) may suitably include pillars disposed upstream, within, or downstream from the channels.

Additional Embodiments

The nanochannel array forms the active region of the device. Here the DNA is analyzed. The patterning, width, depth, pitch, density, length, and area of the array can vary greatly. The nanochannels can be from about 10 nm to about 500 nm deep, with a width of about 10 to about 1000 nm. The nanochannel widths and depths can remain constant through-out the device, or vary, either along the channels, among the channels, or both. The nanochannels can be separated by a distance anywhere from 10 nm to 10 cm, can be anywhere from 0.1 micron to 50 cm in length, and the array can span anywhere from 0.1 micron to 50 cm across. The channels can be parallel, or non-parallel. They do not have to uniformly distributed. They can be of identical length, or of differing lengths. They can be straight, or have turns and curves. They can be isolated from one-another, or intersect.

Primary channels of the branched structures may be separated by distances in the range of from about 1 micron to 50 microns, 100 microns, 1000 microns, or 10 cm. The optimal pitch (spacing) between channels will depend on the needs of the user, and can be identified without difficulty by those of skill in the art.

In one example embodiment the nanochannels are patterned in a parallel array, with a depth of 20-500 nm, and a width of 20-800 nm. For a particular device, the nanochannel's width and depth are constant. The nanochannels are spaced 100 to 2000 nm apart, and are straight. The length of the nanochannels vary from 50 microns to 5000 microns. However, a variety of different nanochannel array embodiments can be realized, including embodiments where a nanochannel's width, depth, or both may vary along the length of the nanochannel.

Interconnects

The interconnect fluidics can have a depth of 100 nm to 100 micron, and a width of 0.5 micron to 1000 microns. In one example embodiment, the depth ranges from 200 nm to 20 micron, and the width ranges from 1 micron to 50 microns.

Additional Description

In some embodiments, the present invention describes a fluidic device including a substrate (A) bonded to a secondary substrate (B), either or both of which may be patterned. The fabrication process describes the micro- and nanofluidic elements that are confined by a bonding process, such as anodic bonding, between the silicon substrate to a glass substrate.

The active region of the chip is suitably located at the interface of the two substrates, where a single or multiple independent nanochannel array devices are fabricated on one or both of the substrate surfaces. These devices are suitably in fluid communication with the environment exterior to the chip via conduit ports extending through one or both substrates.

The disclosed devices suitably include:

Nanochannel Region—The core device region: Here the macromolecule (e.g., DNA) of interest is elongated, linearized, imaged and analyzed.

Gradient Front-End (FE) and Back-end (BE)—An array of interconnected branched channels with cross sectional dimensions ranging from micron, submicron, or in the nanometers range. The FE or BE can also include repeating micro- to nanoscale sized structures such as posts, pillars, wells, grooves, and the combination of the above, which structures interfaces microfluidic and nanofluidic regions of the devices.

Interconnect—The microfluidic region: A network of microfluidic channels that bring the sample of interest from the input ports to the FE region, and provide a conduit for the sample to move from the BE region to the output ports.

Ports: Holes suitably etched through the substrate(s), allowing fluidic communication from the environment exterior to the device to nanofluidic devices (suitably disposed between the substrate A and B) inside the chip through a three dimensional fluidic connection.

A variety of materials can compose the surface of the fluidic elements, including, but not limited to: Silicon, Silicon Dioxide, silicon nitride, hafnium oxide, quartz, glass, fused silica, metal, aluminum oxide, metal, ceramic, polymer, plastic, dielectrics, SiGe, GaAs, GaAlAs, ITO, organic molecules, self-assembled monolayers, self-assembled multi-layers, or any combination thereof.

The present invention discloses devices with all fluidic elements have a dielectric surface by atomic layer deposition (ALD), Pressure Enhanced Chemical Vapor Deposition (PECVD), sputtering, thermo growth, or other entropic or anisotropic material deposition methods. This step provides insulation for electric field manipulation of biological molecules in the fluidic elements as well as further reduction of the fluidic channel manufactured by conventional fabrication methods.

The present invention also discloses nanofluidic element surfaces that can be functionalized and or passivated as required by the application, which surfaces can be transparent to a wide spectrum of electromagnetic radiation, including UV, visible and infrared light.

The nanofluidic devices may also have multiple ports, and can include interfacing, progressively branched channel pattern design having various specifications and angles, as shown in the included figures.

Devices with interfacing progressively branched channel patterns with various branching fork specification and angles. Various combinations of branching channels and post or pillar arrays may also be used to interface between different regions of the disclosed devices, and may also be used as interfaces between channels having different widths.

What is claimed:

1. An analysis device, comprising:
   a first substrate;
   a second substrate;
   a first thin film surmounting at least a portion of the first substrate, the second substrate, or both, wherein the first thin film prevents a fluorescent molecule disposed within the device from being quenched by the first substrate, second substrate, or both; and
   a first inlet port extending through at least a portion of the first substrate, the second substrate, or both, so as to place a first interconnector channel in fluid communication with the environment exterior to the analysis device; and
   a first front-end branched channel region, comprising at least a primary channel characterized as having a cross-sectional dimension of less than about 10,000 nm and at least two secondary channels, placing the first interconnector channel into fluid communication with a nanochannel analysis region,
   the nanochannel analysis region comprising a plurality of nanochannels, wherein the length of each nanochannel is from about 0.1 micron to about 50 cm, and wherein the ratio of the cross-sectional dimensions of the primary channel to the cross-sectional dimensions of each nanochannel is in the range of from about 100 to about 10,000.

2. The analysis device of claim 1, wherein the first substrate, the second substrate, or both, comprises silicon, SiGe, Ge, strained silicon, GeSbTe, AlGaAs, AlGaInP, AlGaN, AlGaP, GaAsP, GaAs, GaN, GaP, InAlAs, InAlP, InSb, GaInAlAs, GaInAlN, GaInAsN, GaInAsP, GaInAs, GaInN, GaInP, GaSb, InN, InP, CdSe, CdTe, zinc selenide (ZnSe), HgCdTe, ZnO, ZnTe, zinc sulfide (ZnS), aluminum, aluminum oxide, stainless steel, Kapton™, metal, ceramic, plastic, polymer, sapphire, silicon carbide, silicon on insulator (SOI), astrositial, barium borate, barium fluoride, sillenite crystals BGO/BSO/BTO, bismuth germanate, calcite, calcium fluoride, cesium iodide, FeILiNbO3, fused quartz, quartz, fused silica, glass, SiO2, gallium, gadolinium garnet, potassium dihydrogen phosphate (KDP), KRS-5, potassium titanyl phosphate, lead molibdate, lithium fluoride, lithium iodate, lithium niobate, lithium tantalate, magnesium fluoride, potassium bromide, titanium dioixde, sodium chloride, tellurium dioxide, spin-on glass, UV curable materials, soda lime glass, any compound above in an hydrogenated form, stoichiometric variations of the above compounds, or any combinations thereof.

3. The analysis device of claim 1, wherein the first substrate comprises a thickness of about 10 nm to about 10,000 nm.

4. The analysis device of claim 1, wherein the first front-end branched channel region comprises a splitter structure dividing the primary channel into least two secondary channels.

5. The analysis device of claim 4, wherein the splitter structure comprises at least one surface angled in the range of from about 0 and about 90 degrees relative to the centerline of the primary channel.

6. The analysis device of claim 4 wherein the width of each secondary channel is about 30% to about 70% of the width of the primary channel.

7. The analysis device of claim 4, wherein the length of a secondary channel is about 1 micron to about 500 microns.

8. The analysis device of claim 4, wherein each of the secondary channel is divided into two tertiary channels by a splitter comprising at least one surface angled in the range of from about 0 and about 90 degrees relative to the centerline of the secondary channel.

9. The analysis device of claim 4, wherein the splitter is configured so as to define an overhang that shields at least a portion of the secondary channel from the primary channel.

10. The analysis device of claim 1, wherein at least one of the plurality of nanochannels comprises a varying width, a varying depth, or both.

11. The analysis device of claim 1, wherein the ratio of a cross-sectional dimension of the port to a cross-sectional dimension of each of the plurality of nanochannels is in the range of from about 1 to about $10^7$.

12. The analysis device of claim 1, wherein the length of each of the plurality of nanochannels is from about 50 microns to about 5000 microns.

13. The analysis device of claim 4, wherein the splitter structure comprises a contoured portion.

14. The analysis device of claim 13, wherein the splitter structure is configured such that a fluidborne body propelled through the primary channel by a gradient is essentially equally likely to enter either secondary channel downstream from the splitter structure.

15. The analysis device of claim 9, wherein the overhang is about 5% to about 50% of the width of the secondary channel.

16. The analysis device of claim 9, wherein the width of a secondary channel is about 30% to about 70% of the width of the primary channel.

17. The analysis device of claim 1, wherein the first thin film comprises a material selected from the group consisting of silicon nitride, silicon oxynitride, SiOxNy, hydrogenated silicon dioxide, hydrogenated silicon nitride, hydrogenated silicon oxinitride, high K dielectrics, TiSiO, TiO, TiN, titanium oxides, hydrogenatedtitanium oxides, titanium nitrides, hydrogenated titanium nitrides, TaO, TaSiO, TaOxNy, $Ta_2O_5$, TaCN, tantalum oxides, hydrogenated tantalum oxides, tantalum nitrides, hydrogenated tantalum nitrides, $HfO_2$, $HfSiO_2$, HfZrOx, HfN, HfON, HfSiN, HfSiON, hafnium oxides, hydrogenated hafnium oxides, hafnium nitrides, hydrogenated hafnium nitrides, ZrO2, ZrSiO2, ZrN, ZrSiN, ZrON, ZrSiON, zirconium oxides, hydrogenated zirconium oxides, zirconium nitrides, hydrogenated zirconium nitrides, $Al_2O_3$, AlN, TiAlN, TaAlN, WAlN, aluminum oxides, hydrogenated aluminum oxides, aluminum nitrides, hydrogenated aluminum nitrides, SiN, WN, low K dielectrics, fluorine doped silicon dioxide, carbon doped silicon dioxide, porous silicon dioxide, porous carbon doped silicon dioxide, spin-on organic polymeric dielectrics, graphite, graphene, carbon nano-tubes, plastics, polymer, organic molecules, self-assembled monolayers, self-assembled multi-layers, a lipid bi-layer, any of the aforementioned compounds in a hydrogenated form, a stoichiometric variation of any of the foregoing, and any combination thereof.

18. The analysis device of claim 1, wherein the first thin film comprises silicon nitride.

19. The analysis device of claim 1, wherein the first thin film surmounts a portion of the first substrate.

20. The analysis device of claim 1, wherein the first thin film surmounts a portion of the second substrate.

21. The analysis device of claim 1, wherein the first thin film defines at least a portion of a channel disposed between the first substrate and the second substrate.

22. The analysis device of claim 1, wherein at least one of the first or second substrates permitting at least partial passage of electromagnetic radiation characterized as having at least one wavelength in the range of from about 10 nm to about 2500 nm.

23. The analysis device of claim 22, wherein the first thin film reduces the background signal of the device when the device is illuminated by electromagnetic radiation of the excitation wavelength.

24. The analysis device of claim 22, wherein the first substrate, the second substrate, or both, comprises silicon.

* * * * *